United States Patent
Snow et al.

(10) Patent No.: US 8,956,818 B2
(45) Date of Patent: Feb. 17, 2015

(54) PROTEOGLYCAN SPLICE VARIANTS AS THERAPEUTICS AND DIAGNOSTICS FOR AMYLOID DISEASES

(75) Inventors: Alan D. Snow, Lynnwood, WA (US); Qubai Hu, Kirkland, WA (US); Judy A. Cam, Bellevue, WA (US); Joel Cummings, Seattle, WA (US)

(73) Assignee: ProteoTech Inc., Kirkland, WA (US)

( * ) Notice: Subject to any disclaimer, the term of this patent is extended or adjusted under 35 U.S.C. 154(b) by 275 days.

(21) Appl. No.: 12/941,279

(22) Filed: Nov. 8, 2010

(65) Prior Publication Data

US 2011/0275080 A1 Nov. 10, 2011

Related U.S. Application Data

(62) Division of application No. 12/394,988, filed on Feb. 27, 2009, now abandoned.

(60) Provisional application No. 61/031,828, filed on Feb. 27, 2008.

(51) Int. Cl.
| | | |
|---|---|---|
| *C12Q 1/68* | (2006.01) | |
| *C07H 21/04* | (2006.01) | |
| *C07K 14/705* | (2006.01) | |
| *C07K 16/28* | (2006.01) | |

(52) U.S. Cl.
CPC ............ *C12Q 1/6883* (2013.01); *C07K 14/705* (2013.01); *C07K 16/2896* (2013.01); *C12Q 2600/158* (2013.01); *C12Q 2600/106* (2013.01); *C12Q 2600/136* (2013.01); *C12Q 2600/156* (2013.01); *C07K 2317/34* (2013.01)
USPC ...... 435/6.12; 435/6.17; 536/23.5; 536/24.33

(58) Field of Classification Search
None
See application file for complete search history.

(56) References Cited

PUBLICATIONS

Verbeek et al. American Journal of Pathology (1999) 155(6): 2115-2125.*
Agrawal et al. Human Molecular Genetics (2006) 15(5): 777-787.*
Fehlbaum-Beurdeley et al. Alzheimer's & Dementia (2010) 6: 25-38.*
Williams et al. Glia (2005) 49: 520-541.*
Pajares et al. Lancet Oncology (2007) 8: 349-357.*
Brinkman Clinical Biochemistry (2004) 37(7): 584-594.*
Perrin et al. Nature (2009) 461: 916-922.*
Kokenyesi, R. Journal of Cellular Biochemistry (2001) 83: 259-270.*
GenBank Accession No. NM_002998 (2003).*
Lowe et al. Nucleic Acids Research (1990) 18(7): 1757-1761.*
Gibson et al. Genome Research (1996) 6: 995-1001.*
Clasper et al. Journal of Biological Chemistry (1999) 274: 24113-24123.*

* cited by examiner

*Primary Examiner* — Angela M Bertagna
(74) *Attorney, Agent, or Firm* — Rebecca Eagen

(57) ABSTRACT

The identification of novel Syndecan-2 splice variants and their use in the diagnosis and therapeutic intervention of Alzheimer's disease and other amyloid diseases. In addition the use of new animal models expressing or devoid of syndecan-2 splice variants to effectively screen and identify potential therapeutic compounds for Alzheimer's disease.

4 Claims, 9 Drawing Sheets

MRRAWILLTLGLVACVSAESNTTAVKGEDAERSGSGLGLGHLQGTR
FLSGIRRAPLYKRHPTGTANISGTFQRAELTSDKDMYLDNSSIEEAS
GVYPIDDDYASASGSGADEDVESPELTTSRPLPKILLTSAAPKVET
TTLNIQNKIPAQTKSPEETDKEKVHLSDSERKMDPAEEDTNVYTEKH
SDSLFKRTEVLAAVIAGGVIGFLFAIFLILLLVYRMRKKDEGSYDLGE
RKPSSAAYQKAPTKEFYA*

Figure 5

```
                        SEQUENCE LISTING

<160> NUMBER OF SEQ ID NOS: 9

<210> SEQ ID NO 1
<211> LENGTH: 18
<212> TYPE: DNA
<213> ORGANISM: Homo sapiens

<400> SEQUENCE: 1
caggaggctt cgttttgc                                                        18

<210> SEQ ID NO 2
<211> LENGTH: 18
<212> TYPE: DNA
<213> ORGANISM: Homo sapiens

<400> SEQUENCE: 2
tcaagggaga ggacgcag                                                        18

<210> SEQ ID NO 3
<211> LENGTH: 19
<212> TYPE: DNA
<213> ORGANISM: Homo sapiens

<400> SEQUENCE: 3
aaggtgccac tgatgttgg                                                       19

<210> SEQ ID NO 4
<211> LENGTH: 19
<212> TYPE: DNA
<213> ORGANISM: Homo sapiens

<400> SEQUENCE: 4
ctgagtcaga gaggtgaac                                                       19

<210> SEQ ID NO 5
<211> LENGTH: 19
<212> TYPE: DNA
<213> ORGANISM: Homo sapiens

<400> SEQUENCE: 5
tagagacact aagttggag                                                       19

<210> SEQ ID NO 6
<211> LENGTH: 891
<212> TYPE: DNA
<213> ORGANISM: Homo sapiens

<400> SEQUENCE: 6
gcaggaggct tcgttttgcc ctggttgcaa gcagcggctg ggagcagccg                     50
```

```
gtccctgggg aatatgcggc gcgcgtggat cctgctcacc ttgggcttgg      100
tggcctgcgt gtcggcggag tcgaacacaa cggcggtcaa gggagaggac      150
gcagaaagat caggctcagg cctgggtctt gggcatcttc aaggaactcg      200
ctttctcagt ggtataagaa gagccccact ctataagagg catccgacag      250
gaacagccaa catcagtggc accttccaaa gagcagagct gacatctgat      300
aaagacatgt accttgacaa cagctccatt gaagaagctt caggagtgta      350
tcctattgat gacgatgact acgcttctgc gtctggctcg ggagctgatg      400
aggatgtaga gagtccagag ctgacaacat ctcgaccact tccaaagata      450
ctgttgacta gtgctgctcc aaaagtggaa accacgacgc tgaatataca      500
gaacaagata cctgctcaga caaagtcacc tgaagaaact gataaagaga      550
aagttcacct ctctgactca gaaggaaaaa tggacccagc cgaagaggat      600
acaaatgtgt atactgagaa acactcagac agtctgttta aacggacaga      650
agtcctagca gctgtcattg ctggtggagt tattggcttt ctctttgcaa      700
tttttcttat cctgctgttg gtgtatcgca tgagaaagaa ggatgaagga      750
agctatgacc ttggagaacg caaaccatcc agtgctgctt atcagaaggc      800
acctactaag gagttttatg cgtaaaactc aacttagtg tctctattta      850 tgagatcact gaacttttca aaataaagct tttgcataga a              891
```

<210> SEQ ID NO 7
<211> LENGTH: 253
<212> TYPE: PRT
<213> ORGANISM: Homo sapiens

<400> SEQUENCE: 7

```
Met Arg Arg Ala Trp Ile Leu Leu Thr Leu Gly Leu Val Ala Cys
 1               5                  10                  15

Val Ser Ala Glu Ser Asn Thr Thr Ala Val Lys Gly Glu Asp Ala
            20                  25                  30

Glu Arg Ser Gly Ser Gly Leu Gly Leu Gly His Leu Gln Gly Thr
            35                  40                  45

Arg Phe Leu Ser Gly Ile Arg Arg Ala Pro Leu Tyr Lys Arg His
            50                  55                  60

Pro Thr Gly Thr Ala Asn Ile Ser Gly Thr Phe Gln Arg Ala Glu
            65                  70                  75

Leu Thr Ser Asp Lys Asp Met Tyr Leu Asp Asn Ser Ser Ile Glu
            80                  85                  90

Glu Ala Ser Gly Val Tyr Pro Ile Asp Asp Asp Tyr Ala Ser
            95                 100                 105

Ala Ser Gly Ser Gly Ala Asp Glu Asp Val Glu Ser Pro Glu Leu
           110                 115                 120

Thr Thr Ser Arg Pro Leu Pro Lys Ile Leu Leu Thr Ser Ala Ala
           125                 130                 135

Pro Lys Val Glu Thr Thr Thr Leu Asn Ile Gln Asn Lys Ile Pro
           140                 145                 150

Ala Gln Thr Lys Ser Pro Glu Glu Thr Asp Lys Glu Lys Val His
           155                 160                 165

Leu Ser Asp Ser Glu Arg Lys Met Asp Pro Ala Glu Glu Asp Thr
           170                 175                 180
```

```
Asn Val Tyr Thr Glu Lys His Ser Asp Ser Leu Phe Lys Arg Thr
                185                 190                 195

Glu Val Leu Ala Ala Val Ile Ala Gly Gly Val Ile Gly Phe Leu
                200                 205                 210

Phe Ala Ile Phe Leu Ile Leu Leu Leu Val Tyr Arg Met Arg Lys
                215                 220                 225

Lys Asp Glu Gly Ser Tyr Asp Leu Gly Glu Arg Lys Pro Ser Ser
                230                 235                 240

Ala Ala Tyr Gln Lys Ala Pro Thr Lys Glu Phe Tyr Ala
                245                 250

<210> SEQ ID NO 8
<211> LENGTH: 156
<212> TYPE: DNA
<213> ORGANISM: Homo sapiens

<400> SEQUENCE: 8
aacacaacgg cggtcaaggg agaggacgca gaaagatcag gctcaggcct        50
gggtcttggg catcttcaag gaactcgctt tctcagtggt ataagaagag       100
ccccactcta taagaggcat ccgacaggaa cagccaacat cagtggcacc       150
ttccaa                                                       156

<210> SEQ ID NO 9
<211> LENGTH: 52
<212> TYPE: PRT
<213> ORGANISM: Homo sapiens

<400> SEQUENCE: 9

Asn Thr Thr Ala Val Lys Gly Glu Asp Ala Glu Arg Ser Gly Ser
 1               5                  10                  15

Gly Leu Gly Leu Gly His Leu Gln Gly Thr Arg Phe Leu Ser Gly
                20                  25                  30

Ile Arg Arg Ala Pro Leu Tyr Lys Arg His Pro Thr Gly Thr Ala
                35                  40                  45

Asn Ile Ser Gly Thr Phe Gln
                50
```

PROTEOGLYCAN SPLICE VARIANTS AS THERAPEUTICS AND DIAGNOSTICS FOR AMYLOID DISEASES

RELATED APPLICATIONS

This application is a division of U.S. application Ser. No. 12/394,988 filed Feb. 27, 2009, now abandoned, which claims priority to U.S. provisional application No. 61/031,828 filed Feb. 27, 2008.

TECHNICAL FIELD

This invention relates to the discovery and identification of novel proteoglycan splice variants and their utilization for the diagnosis and therapeutic intervention of Alzheimer's disease and other amyloid diseases. In addition new animal models to effectively screen and identify potential therapeutic compounds for Alzheimer's disease and each of the amyloidoses are described.

BACKGROUND OF THE INVENTION

Alzheimer's disease (AD) is a degenerative brain disorder characterized clinically by progressive loss of memory, cognition, reasoning, judgment and emotional stability that gradually leads to profound mental deterioration and ultimate death. Alzheimer's disease is the leading cause of dementia in the elderly, affecting 5-10% of the population over the age of 65 years (Jorm A, A Guide to the Understanding of Alzheimer's Disease and Related Disorders, University Press, New York, 1987.). In AD, the parts of the brain essential for cognitive processes such as memory, attention, language, and reasoning degenerate. AD is characterized by the deposition and accumulation of a 39-43 amino acid peptide termed the beta-amyloid protein, Aβ (Glenner G G, and C W Wong. Biochem. Biophys. Res. Comm. 120:885-890, 1984., Husby G, et al. Bull WHO 71:105-108, 1993., Masters C L, et al. Proc. Natl. Acad. Sc. USA 82:4245-4249, 1985.). Aβ is derived from larger precursor proteins termed beta-amyloid precursor proteins (or APPs) of which there are several alternatively spliced variants. The most abundant forms of APPs include proteins consisting of 695, 751 and 770 amino acids (Kitaguchi N, et al. Nature 331:530-532, 1988. Ponte P, et al. Nature 331:525-527, 1988., Tanzi R E, et al. Nature 331:528-530, 1988.). The small Aβ peptide is a major component, which makes up the amyloid deposits of "plaques" in the brains of patients with AD either as extracellular amyloid plaques or in blood vessel walls in the parenchyma. In addition, AD is characterized by the presence of numerous neurofibrillary "tangles", consisting of paired helical filaments (PHFs) that abnormally accumulate in the neuronal cytoplasm (Grundke-Iqbal I, et al. Proc. Natl. Acad. Sci. USA 83:4913-4917, 1986., Kosik K S, et al. Proc. Natl. Acad. Sci. USA 83:4044-4048, 1986., Lee V M Y, et al. Science 251: 675-678, 1991.). The pathological hallmarks of AD are therefore the presence of "plaques" and "tangles" with amyloid being deposited in the central core of plaques. The other major type of lesion found in AD brain is the accumulation of amyloid in the walls of blood vessels, both within the brain parenchyma and in the walls of meningeal vessels that lie outside the brain. Aβ amyloid formation, deposition, accumulation and persistence are believed to play a central role in AD pathogenesis by contributing to neuronal loss and memory dysfunction. The primary factor(s) causing amyloid plaque and NFT accumulation leading to the pathogenesis of AD is not known.

Previous studies indicate that the accumulation of Aβ and amyloid is indeed a causative factor for AD. Aβ in cell culture causes degeneration of nerve cells within short periods of time (Pike C J, et al. Br. Res. 563:311-314, 1991., Pike C J, et al. J. Neurochem. 64:253-265, 1995.). Aβ has been found to be neurotoxic in slice cultures of hippocampus (Harrigan M R, et al. Neurobiol. Aging 16:779-789, 1995.) and induces nerve cell death in some forms of transgenic mice (Games D, et al. Nature 373:523-527, 1995., Hsiao K, et al. Science 274:99-102, 1996, Sturchler-Pierrat C, et al. Proc. Natl. Acad. Sci. 94:13287-13292, 1997.). Previous studies utilizing amyloid plaque producing transgenic mice also clearly demonstrate a direct correlation between increased amyloid plaque burden and behavioral deficits in memory tasks (Choi P Y, et al. Neuroscience Meeting, Orlando, Fla., November 2002., Janus C, et al. Nature 408:979-982, 2000., Morgan D, et al. Nature 408:982-985, 2000.). Probably the most convincing evidence that Aβ amyloid is directly involved in the pathogenesis of AD comes from genetic studies in which the production of Aβ resulted from mutations in the APP gene (Haas C, et al. Nature Med. 1:1291-1296, 1995., Murrell J, et al. Science 254:97-99, 1991., Van Broeckhoven C, et al. Science 248:1120-1122, 1990.), and duplication of the APP locus (Rovelet-Lecrux et al., Nature Genetics, 38:24-26, 2006).

Important amyloid co-factors that may play a role in the pathogenesis of AD are specific proteoglycans (PGs) and glycosaminoglycans (GAGs). Previous studies demonstrated that particular heparan sulfate proteoglycans (HSPGs) including perlecan, syndecan-2, glypican, and agrin are specifically immunolocalized to Aβ-containing amyloid plaques and/or cerebrovascular amyloid deposits in AD brain (Perlmutter L S, et al. Br. Res. 508:13-19, 1990., Snow A D, et al. Am. J. Path. 133:456-463, 1988., Snow A D, and T N Wight, Neurobiol. Aging 10:481-497, 1989., Snow A D, et al. Am. J. Path. 137:1253-1270, 1990., Snow A D, et al. Neuron 12: 219-234, 1994., Su J H, et al. Neurosc. 51:801-813, 1992., Van Gool D, et al. Dementia 4:308-314, 1993., Van Horssen J, et al. Lancet 2:482-492, 2003, Castillo G M, et al. J. Neurochem. 69:2452-2465, 1997., Narindrasorasak S, et al. J. Biol. Chem. 266:12878-12883, 1991., Snow A D, et al. Am. J. Path. 144:337-347, 1994., Snow A D, et al. Arch. Biochem. Biophys. 320:84-95, 1995, Lashley T, et al. Neuropath. Appl. 32:492-504, 2006., Verbeek M M, et al. Am. J. Path. 155: 2115-2125,1999, Lashley T, et al. Neuropath. Appl. 32:492-504, 2006., Verbeek M M, et al. Am. J. Path. 155:2115-2125, 1999., Watson D J, et al. J. Biol. Chem. 272:31617-31624, 1997, Cotman S L, et al. Mol Cell. Neurosc. 15:183-198, 2000., Lashley T, et al. Neuropath. Appl. 32:492-504, 2006., Schultz J G, et al. Europ. J. Neuorsc. 10:2085-2093, 1998., Verbeek M M, et al. Am. J. Path. 155:2115-2125,1999., Watanabe N, et al. FASEB J. published online, Apr. 14, 2004., Watson D J, et al. J. Biol. Chem. 272:31617-31624, 1997). These HSPGs also accumulate in transgenic mice overexpressing beta-amyloid precursor protein (APP) and accumulate in brain concurrent with initial Aβ accumulation and deposition (Cummings J A, et al. Annual Meeting of Neuroscience, Washington, DC, Nov 2005, Snow A D, et al. 8th International Conference on Alzheimer's and Parkinson's disease, Salzburg, Austria, March 2007). It is believed that HSPGs facilitate amyloid deposition and/or promote the persistence of amyloid by inhibiting clearance mechanisms (Snow A D, and T N Wight, Neurobiol. Aging 10:481-497, 1989.).Consistent with this hypothesis in vitro studies have revealed that HSPGs such as perlecan (Narindrasorasak S, et al. J. Biol. Chem. 266:12878-12883, 1991., Snow A D, et al. J. Histochem. Cytochem. 40:105-113, 1992., Snow A D, et al. Arch. Biochem. Biophys. 320:84-95, 1995.), agrin (Cotman S L, et al. Mol Cell. Neurosc. 15:183-198, 2000.) and glypican (Watson D J, et al. J. Biol. Chem. 272:31617-31624, 1997.) can bind with high affinity to Aβ and APPs (Narindrasorasak S, et al. J. Biol. Chem. 266:12878-12883, 1991.). Additionally, in vitro and cell culture studies demonstrate that HSPGs protect Aβ from protease degradation (Gupta-Bansal R, et al. J. Biol. Chem. 270:18666-18671, 1995., Nguyen B P, et al. Annual Meeting of Neuroscience, New Orleans, LO November 2003., Snow A D, et al. Neuron 12: 219-234, 1994.), supporting a role for HSPGs in inhibition of Aβ-degradation and removal in vivo. All of these studies implicate HSPGs as important co-factors postulated to lead to the accumulation and persistence of Aβ. HSPGs are also specifically co-localized to the PHFs in NFTs in AD brain (Snow A D, et al. Acta Neuropath. 78:113-123, 1989., Snow A D and G M Castillo. Amyloid: Int. J. Exp. Clin. Invest. 4:135-141, 1997.). An alternative hypothesis is that PG's may affect APP processing. Our results suggest that syndecan-2 splice variants interfere with β-secretase cleavage of APP which may lead to a reduction in Aβ levels. Studies have also demonstrated that highly sulfated GAGs such as heparan sulfate can induce tau protein to adopt PHF formation identical to that observed in AD brain (Friedrich M V, et al. J. Biol. Chem. 294:259-270, 1999., Goedert M, et al. Nature 383:550-553, 1996., Hasegawa M, et al. J. Biol. Chem. 272:33118-33124, 1997., Perez M, et al. J. Neurochem. 67:1183-1190, 1996.). Our results also support that syndecan-2 splice variants may be relevant to tau NFT formation. Therefore, HSPGs may play an important role in the pathology of AD.

Proteoglycans (PGs) usually consist of a protein core to which are covalently attached one or more glycosaminoglycan (GAG) chains. GAGs consist of a repeating disaccharide unit containing a hexuronic acid (either glucuronic acid or iduronic acid) or hexosamine (glucosamine or galactosamine) (reviewed in Snow A D, and T N Wight. Neurobiol. Aging 10:481-497, 1989). Different classes of GAGs include the highly sulfated heparin and heparan sulfate, and the less sulfated keratan sulfate, dermatan sulfate, chondroitin-4-sulfate, chondroitin-6-sulfate, and the non-sulfated hyaluronic acid (reviewed in Snow A D, and T N Wight. Neurobiol. Aging 10:481-497, 1989). At least 4 different classes of PGs have been shown to be present in AD brain. These include heparan sulfate proteoglycans (HSPGs) (Perlmutter L S, et al. Br. Res. 508:13-19, 1990., Snow A D, et al. Am. J. Path. 133:456-463, 1988., Snow A D, and T N Wight. Neurobiol. Aging 10:481-497, 1989., Snow A D, et al. Am. J. Path. 137:1253-1270, 1990., Snow A D, et al. Neuron 12: 219-234, 1994., Su J H, et al. Neurosc. 51:801-813, 1992., Van Gool D, et al. Dementia 4:308-314, 1993. Van Horssen J, P et al. Lancet 2:482-492, 2003.), dermatan sulfate PGs (Snow A D, et al. J. Histochem. Cytochem. 40:105-113, 1992), chondroitin sulfate PGs (DeWitt D A, et al. Exp. Neurol. 121:149-152, 1993.) and keratan sulfate PGs (Snow A D, et al. Exp. Neurol. 138:305-317, 1996.). Of all these different PGs, evidence indicated that only the HSPGs are specifically immunolocalized to the Aβ-containing fibrils both in the amyloid plaques and in the cerebrovascular amyloid deposits in AD brain (Perlmutter L S, et al. Br. Res. 508:13-19, 1990, Snow A D, et al. Am. J. Path. 133:456-463, 1988, Snow A D, and T N Wight. Neurobiol. Aging 10:481-497, 1989., Snow A D, et al. Am. J. Path. 137:1253-1270, 1990, Snow A D, et al. Neuron 12: 219-234, 1994., Su J H, et al. Neurosc. 51:801-813, 1992, Van Gool D, et al. Dementia 4:308-314, 1993. Van Horssen J, et al. Lancet 2:482-492, 2003.). Particular HSPGs that have been immunolocalized or identified within Aβ-amyloid deposits in AD brain include perlecan (Castillo et al. J. Neurochem. 69:2452-2465, 1997, Narindrasorasak S, et al. J. Biol. Chem. 266:12878-12883, 1991, Snow A D, et al. Am. J. Path. 144:337-347, 1994, Snow A D, et al. Arch. Biochem. Biophys. 320:84-95, 1995), syndecan-2 (Lashley T, et al. Neuropath. Appl. 32:492-504, 2006, Verbeek M M, et al. Am. J. Path. 155:2115-2125, 1999), agrin (Cotman S L, et al. Mol Cell. Neurosc. 15:183-198, 2000, Lashley T, et al. Neuropath. Appl. 32:492-504, 2006, Verbeek M M, et al. Am. J. Path. 155:2115-2125,1999), and glypican (Lashley T, et al. Neuropath. Appl. 32:492-504, 2006, Schultz J G, et al. Europ. J. Neuorsc. 10:2085-2093, 1998, Verbeek M M, et al. Am. J. Path. 155:2115-2125,1999., Watanabe N, et al. FASEB J. published online, Apr. 14, 2004., Watson D J, et al. J. Biol. Chem. 272:31617-31624, 1997.). Our own studies indicate that HSPGs, such as perlecan (which consists of a ~400 kDa core protein with 3 heparan sulfate GAG chains attached) are integral parts of amyloid deposits in AD brain. Perlecan is present in isolated amyloid plaque core preparations derived from AD brain as determined by positive immunostaining and western blotting with specific perlecan core protein antibodies (Castillo G M, et al. Soc. Neurosc. Abstr. 22:1172, 1996, Castillo G M, et al. 6th International Conference on Alzheimer's Disease and Related Disorders, Amsterdam, July 1998). Perlecan, syndecan-2, glypican and agrin all not only co-localized to Aβ-amyloid deposits in AD brain, but are also present and co-immunolocalized to amyloid plaques in APP transgenic mice (Cummings J A, et al. Annual Meeting of Neuroscience, Washington, DC, November 2005, Snow A D, et al. 8th International Conference on Alzheimer's and Parkinson's disease, Salzburg, Austria, March 2007). In fact, HS GAGs accumulate in APP mouse brain concurrent and co-localized with initial Aβ accumulation and deposition in brain tissue (Cummings J A, et al. Annual Meeting of Neuroscience, Washington, DC, November 2005, Snow A D, et al. 8th International Conference on Alzheimer's and Parkinson's disease, Salzburg, Austria, March 2007). HSPG immunoreactivity is localized to diffuse plaques in AD (Snow A D, et al. Am. J. Path. 133:456-463, 1988, Snow A D, et al. Am. J. Path. 137:1253-1270, 1990., Snow A D, et al. Am. J. Path. 144:337-347, 1994.) and Down's syndrome brain (Snow A D, et al. Am. J. Path. 137:1253-1270, 1990.) suggesting that this particular class of PGs may-in fact represent a primary initiating factor leading to Aβ accumulation and persistence. Consistent with this hypothesis is the observation that in very young Down's syndrome brain (as early as 1 day after birth), marked HS accumulation in neuronal cytoplasm occurs prior and much earlier than the first appearance of Aβ-deposition (in neurons and later in the matrix) and fibrillar amyloid (Snow A D, et al. Am. J. Path. 137:1253-1270, 1990.). In other types of amyloidosis (such as systemic AA amyloidosis) where the temporal relationship in the experimental mouse model has been extensively studied, it is clear that an increase in gene expression of specific HSPGs, such as perlecan, occurs prior to AA amyloid formation and deposition in tissues (Ailles L, et al., Lab. Invest. 69:443-448, 1993, Elimova E, et al. FASEB J. 18:1749-1751, 2004, Snow A D, and R Kisilevsky, Lab. Invest. 53:37-44, 1985). Furthermore, heparanase overexpressing transgenic mice that cause a decrease in HS accumulation renders mice resistant to induction of systemic AA amyloidosis (Li J P, et al. Proc. Natl. Acad. Sc. 102:6473-6477, 2005) further supporting an important role of HSPGs for the induction of amyloidosis.

Perlecan is a large HSPG normally present on all basement membranes, consisting of 94 exons, coding for a large ~470 kDa protein core. Perlecan core protein contains a cluster of 3 GAG attachment sites in domain I (Dolan M, et al., J. Biol. Chem. 272:4316-4322, 1997, Murdoch A D, et al., J. Biol. Chem. 267:8544-8557, 1992). Possible splice variants of perlecan have been reported for mammalian perlecan (Joseph S J, et al., Develop. 122:3443-3452, 1996.). Syndecan-2 is one of four members of this single-pass transmembrane family in vertebrates (Kramer K L, and H J Yost, Ann. Rev. Gen. 37:461-484, 2003). The ~22 kDa core protein is organized into 3 regions: the N-terminal ectodomain containing a signal sequence, followed by 3 predicted GAG attachment sites, a transmembrane domain and a highly conserved cytoplasmic domain (reviewed in Essner J J, et al. Int. J. Biochem. Cell Biol. 38:152-156, 2006).

The HSPGs, perlecan (Castillo G M, et al. J. Neurochem. 69:2452-2465, 1997., Narindrasorasak S, et al. J. Biol. Chem. 266:12878-12883, 1991, Snow A D, et al. Am. J. Path. 144: 337-347, 1994., Snow A D, et al. Arch. Biochem. Biophys. 320:84-95, 1995.), syndecan-2 (Lashley T, et al. Neuropath. Appl. 32:492-504, 2006., Verbeek M M, et al. Am. J. Path. 155:2115-2125,1999), agrin (Cotman S L, et al. Mol Cell. Neurosc. 15:183-198, 2000., Lashley T, et al. Neuropath. Appl. 32:492-504, 2006, Schultz J G, et al. Europ. J. Neuorsc. 10:2085-2093, 1998, Verbeek M M, et al. Am. J. Path. 155: 2115-2125,1999, Watanabe N, et al. FASEB J. published online, Apr. 14, 2004., Watson D J, et al. J. Biol. Chem. 272:31617-31624, 1997.) and glypican (Lashley T, et al. Neuropath. Appl. 32:492-504, 2006., Schultz J G, et al. Europ. J. Neuorsc. 10:2085-2093, 1998, Verbeek M M, et al. Am. J. Path. 155:2115-2125,1999., Watanabe N, et al. FASEB J. published online, Apr. 14, 2004., Watson D J, et al. J. Biol. Chem. 272:31617-31624, 1997.) have been specifically immunolocalized to amyloid plaques in AD brain. In addition, our studies have identified these same HSPGs in the amyloid plaque deposits in APP mouse transgenic brain (FIG. 1) (Cummings J A, et al. Annual Meeting of Neuroscience, Washington, DC, November 2005, 102, Snow A D, et al. 8th International Conference on Alzheimer's and Parkinson's disease, Salzburg, Austria, March 2007). Sulfated GAGs and polyanions also play a role in PHF formation such as observed in NFTs in AD brain. In early studies by Snow et al (Snow A D, et al. Acta Neuropath. 78:113-123, 1989.) cationic dyes retained PGs in tissues and at the electron microscopic level it was clear that PGs were specifically co-localized to the PHFs in NFTs, in a specific periodic fashion. HSPG antibodies also immunolocalized HSPGs to tangles in AD brain (Goedert M, et al. Nature 383:550-553, 1996, Snow A D, and T N Wight. Neurobiol. Aging 10:481-497, 1989., Snow A D, et al. Am. J. Path. 137:1253-1270, 1990., Snow A D and G M Castillo. Amyloid: Int. J. Exp. Clin. Invest. 4:135-141, 1997.). Evidence by a number of groups later confirmed that highly sulfated GAGs (i.e. heparan sulfate and heparin) were potent inducers of tau polymerization into PHFs (Friedhoff P, et al., Biochem. 37:10223-10230, 1998. Goedert M, et al. Nature 383:550-553, 1996, Hasegawa M, et al. J. Biol. Chem. 272:33118-33124, 1997, Perez M, et al. J. Neurochem. 67:1183-1190, 1996). Since heparin is only found primarily in mast cells (not in brain tissue), it is postulated that the heparan sulfate class of PGs are important in the induction of PHFs as observed in AD brain.

Syndecan-2 is widely expressed in many tissues including brain. In neurons, syndecan-2 is concentrated at synapses in dimer/multimer clusters playing an essential role in creating specialized membrane environments for post-synaptic signaling (Ethell I M, et al., Neuron 31:1001-1013, 2001). The human syndecan-2 transcript consists of 5 exons, coding for a 22 kDa protein product that has 201 residues. The first of the GAG attachment sites in syndecan-2 is encoded by exon 2 and the other 2 GAG attachment sites, representing adjacent duplicate SG amino acid residues with a flanking cluster of acidic residues encoded by the combined sequence derived from the boundary of exons 2/3.

Agrin is also a large PG with the gene encoding a protein with a predicted MW of 225 kDa. At least 3 HS GAG attachment sites are present in the amino-terminal half of agrin (Hoch W, et al., EMBO J. 13:2814-2821, 1994., Tsen G, et al., J. Biol. Chem. 270:3392-3399, 1995.). The extensive glycosylation in this region increases the apparent molecular mass of agrin to 600 kDa. The C-terminal half of agrin is active in acetylcholine receptor aggregation and contains binding sites for dystroglycan, heparin and some integrins (Bezakova G, and M A Ruegg, Nat. Rev. Mol. Cell Biol. 4:295-308, 2003.). Agrin is expressed as several isoforms in various tissues.

Six different glypicans have been identified in mammals (Esko J D, and S B Selleck, Ann. Rev. Biochem. 71:435-471, 2002.); they are encoded by 6 independent genes that contain 8-12 exons. All glypicans are approximately 60-70 kDa in size. The GAG attachment sites are usually identified as a cluster, which locate within the last 50 residues at the C-terminus, next to a glyosylphosphotidy-linositol membrane anchor (Kramer K L, and H J Yost, Ann. Rev. Gen. 37:461-484, 2003., Veugelers M, et al., J. Biol. Chem., 274:26969-26977, 1999.).

It is believed that HSPGs facilitate Aβ to ultimately adapt a beta-sheet conformation and into insoluble amyloid fibrils. Consistent with this hypothesis, HSPGs such as perlecan (Narindrasorasak S, et al. J. Biol. Chem. 266:12878-12883, 1991., Snow A D, et al. J. Histochem. Cytochem. 40:105-113, 1992., Snow A D, et al. Arch. Biochem. Biophys. 320:84-95, 1995.), agrin (Dolan M, et al. J. Biol. Chem. 272:4316-4322, 1997.) and glypican (Watson D J, et al. J. Biol. Chem. 272: 31617-31624, 1997.) can bind with high affinity to AB and APPs (Narindrasorasak S, et al. J. Biol. Chem. 266:12878-12883, 1991). In addition, HSPGs, such as perlecan, enhance fibrillar Aβ amyloid deposition and persistence in brain, when co-infused with Aβ into rodent hippocampus (Snow A D, et al. Neuron 12: 219-234, 1994.). Furthermore, perlecan and HS GAGs can induce Aβ 1-40 peptides in vitro to adopt a congophilic Maltese-cross spherical plaque core appearance identical to that observed in AD brain (Choi P Y, et al. Neuroscience Meeting, Orlando, Fla., November 2002., Snow A D, et al. 10$^{th}$ International Symposium on Amyloid and Amyloidosis, Tours, France, April 2004.). These studies implicate HSPGs as important co-factors that may lead to the accumulation and persistence of Aβ. Studies indicate that the highly sulfated GAG chains (and not the core protein) are critical for formation and acceleration of Aβ amyloid (as observed in "plaques") (Castillo G M, et al. J. Neurochem. 72:1681-1687, 1999), and for tau protein to form PHFs (as observed in "tangles") (Friedrich M V, et al. J. Biol. Chem. 294:259-270, 1999, Goedert M, et al. Nature 383:550-553, 1996, Hasegawa M, et al. J. Biol. Chem. 272:33118-33124, 1997, Perez M, et al. J. Neurochem. 67:1183-1190, 1996). In one study, heparin/HS GAGs in which the sulfate moieties had been removed, demonstrated a nearly complete loss of the GAG's ability to accelerate Aβ amyloid fibril formation (Castillo G M, et al. J. Neurochem. 72:1681-1687, 1999). Thus it is postulated that any increase in HS GAG number, leads to an overall increase in GAG sulfation, which is critical to cause a formation and acceleration of both Aβ amyloid fibril and PHF formation in AD. Studies are therefore needed that characterize the degree of sulfation in PG GAGs and elucidate the role of sulfation in Aβ amyloid fibril and PHF formation in AD.

Amyloid as a Therapeutic Target for Alzheimer's Disease

Alzheimer's disease is characterized by the deposition and accumulation of a 39-43 amino acid peptide termed the beta-amyloid protein, Aβ or β/A4 (Glenner and Wong, *Biochem.*

Biophys. Res. Comm. 120:885-890, 1984; Masters et al., Proc. Natl. Acad. Sci. USA 82:4245-4249, 1985; Husby et al., Bull. WHO 71:105-108, 1993). Aβ is derived by protease cleavage from larger precursor proteins termed β-amyloid precursor proteins (APPs) of which there are several alternatively spliced variants. The most abundant forms of the APPs include proteins consisting of 695, 751 and 770 amino acids (Tanzi et al., Nature 31:528-530, 1988).

The small Aβ peptide is a major component that makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., Proc. Natl. Acad. Sci. USA 83:4913-4917, 1986; Kosik et al., Proc. Natl. Acad. Sci. USA 83:4044-4048, 1986; Lee et al., Science 251:675-678, 1991). The pathological hallmark of Alzheimer's disease is therefore the presence of "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, J. Neuropath. Exp. Neurol. 45:79-90, 1986; Pardridge et al., J. Neurochem. 49:1394-1401, 1987)

For many years there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al., Br. Res. 563:311-314, 1991; J. Neurochem. 64:253-265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al., Neurobiol. Aging 16:779-789, 1995) and induces nerve cell death in transgenic mice (Games et al., Nature 373:523-527, 1995; Hsiao et al., Science 274:99-102, 1996). Injection of the Alzheimer's Aβ into rat brain also causes memory impairment and neuronal dysfunction (Flood et al., Proc. Natl. Acad. Sci. USA 88:3363-3366, 1991; Br. Res. 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding, its precursor, β-amyloid precursor protein (Van Broeckhoven et al., Science 248:1120-1122, 1990; Murrell et al., Science 254:97-99, 1991; Haass et al., Nature Med. 1:1291-1296, 1995). The identification of mutations in the beta-amyloid precursor protein gene that cause early onset familial Alzheimer's disease is the strongest argument that amyloid is central to the pathogenetic process underlying this disease. Four reported disease-causing mutations have been discovered which demonstrate the importance of Aβ in causing familial Alzheimer's disease (reviewed in Hardy, Nature Genet. 1:233-234, 1992). All of these studies suggest that providing a drug to reduce, eliminate or prevent fibrillar Aβ formation, deposition, accumulation and/or persistence in the brains of human patients will serve as an effective therapeutic.

Modulators of APP Secretases as Therapeutic Targets for Alzheimer's Disease

Elucidating APP metabolism and its role in the formation of Aβ plaques in AD is becoming increasingly important as therapeutics for AD and other beta-amyloid protein diseases are sought. Intracellular trafficking and proteolytic processing of APP directly influences the amount and type of Aβ peptide and can thus have a profound impact on amyloid plaque load.

Processing of APP in vivo and in cultured cells occurs by two major pathways (Haass and De Strooper, Science 286 (5441):916-9 (1999) and; Selkoe, Physiol Rev. 81(2):741-66, (2001)). Cleavage of APP at the N-terminus of the Aβ region by β-secretase and at the C-terminus by γ-secretases represents the amyloidogenic pathway for processing of APP. β-secretase cleaves APP between residues $Met^{595}$ and $Asp^{596}$ (codon numbering refers to the $APP^{695}$ isoform), and yields Aβ peptide plus the β-C-terminal fragment (βCTF or C99). Following β-secretase cleavage, a second cleavage by γ-secretase occurs at the C-terminus of Aβ peptide that releases Aβ from CTF. This cleavage occurs in the vicinity of residue 636 of the C-terminus. γ-secretase can cleave the C-terminal region at either $Val^{636}$ or $Ile^{638}$ to produce a shorter Aβ peptide (Aβ1-40) or the longer Aβ peptide (Aβ1-42). The predominant form of Aβ found in the cerebrospinal fluid and conditioned media of cultured cells is the shorter Aβ40 peptide. Despite its lower abundance, Aβ42 is the peptide that is initially deposited within the extracellular plaques of AD patients. In addition, Aβ42 is shown to aggregate at a much lower concentration than the Aβ40 form. APP can alternatively be processed via a non-amyloidogenic pathway where α-secretase cleaves within the Aβ domain between $Lys^{611}$ and $Leu^{612}$, and produces a large soluble α-APP domain (sAPPα) and a α-C-terminal fragment (αCTF or C83). The latter can then be cleaved by γ-secretase at residue 636 or 638 to release a P3 peptide and the APP intracellular domain (AICD). The α-cleavage pathway is the major pathway used to process APP in vivo; it does not yield Aβ peptide (Selkoe, Physiol Rev. 81(2):741-66, (2001). The characterization of APP cleavage and the related secretases has provided significant advancement in therapeutic strategies that may lead to limiting the deposition of Aβ peptide in the brain, and eliminate or delay the associated pathological effects in AD.

BRIEF SUMMARY OF THE INVENTION

In a first aspect, this invention is the utilization of novel and specific primer sequences for the detection of proteoglycan splice variants in human tissues using standard RT-PCR methodology, known to one skilled in the art. In another aspect, this invention is the utilization of standard RT-PCR methodology, utilizing the specific primers described herein, which will aid in the amplification of each of specific proteoglycan splice variants, for the ultimate detection of these splice variants in various human tissues, cells and in biological fluids. In addition, quantitative competitive RT-PCR techniques can be utilized (Maresh et al, J. Neurochem. 67:1132-1144, 1996) to determine quantitative differences in these specific variants in total RNA derived from human tissues, cells, white blood cells and in biological fluids. Changes in quantitative levels of these specific proteoglycan splice variants will aid in the diagnosis and monitoring of prognosis of patients who demonstrate amyloid and concurrent specific proteoglycan splice variant and/or specific proteoglycan accumulation in tissues as part of the pathological process observed in the amyloid diseases, especially Alzheimer's disease.

In another aspect, this invention is the utilization of the syndecan-2 slice variants as a specific indicator for the presence and progression of Alzheimer's disease and/or other amyloid diseases by monitoring biological fluids including, but not limited to, cerebrospinal fluid, blood, serum, plasma, urine, saliva, sputum, and stool.

In another aspect, this invention is the utilization of the syndecan-2 slice variants as a specific indicator for the presence and progression of Alzheimer's disease and/or other amyloid diseases by monitoring biological fluids including, but not limited to, cerebrospinal fluid, blood, serum,plasma, urine, saliva, sputum, and stool.

In another aspect, this invention is the utilization of purified antibodies to syndecan-2 slice variants as specific indicators for the presence and progression of Alzheimer's disease and/or other amyloid diseases by monitoring brain and biological fluids including, but not limited to, cerebrospinal fluid, blood, serum, urine, saliva, sputum, and stool.

In another aspect, this invention is the utilization of the syndecan-2 slice variants as a specific indicator for the presence and extent of amyloid plaques in brain by monitoring biological fluids including, but not limited to, cerebrospinal fluid, blood, serum, urine, saliva, sputum, and stool.

In another aspect, this invention is the utilization of the syndecan-2 slice variants as therapeutics for Alzheimer's disease due to the effects of syndecan-2 slice variants as modulators of APP processing and the subsequent reduction of beta secretase product.

In another aspect, this invention is the utilization of a method which can evaluate a compound or potential therapeutics' ability to alter (diminish or eliminate) the affinity of a given amyloid protein (as described herein) or amyloid precursor protein, to proteoglycan splice variant protein or proteoglycan splice variant GAGs. By providing a method of identifying compounds which affect the binding of amyloid proteins, or amyloid precursor proteins to such proteoglycan splice variant protein or proteoglycan splice variant derived-GAGs or fragments thereof, the present invention is also useful in identifying compounds which can prevent or impair such binding interaction. Thus, compounds can be identified which specifically affect an event linked with the amyloid formation, amyloid deposition, and/or amyloid persistence condition associated with Alzheimer's disease and other amyloid diseases.

In another aspect, this invention is the utilization of peptides or fragments thereof which are specific against new and unique sequences of any proteoglycan splice variant. These peptides or fragments thereof can be used as potential blocking therapeutics for the interaction of the proteoglycan splice variants in a number of biological processes and diseases (such as in the amyloid diseases described herein).

In another aspect, this invention is the utilization and production of oligonucleotides utilizing the nucleotide sequences described herein, to be utilized as new molecular biological probes to detect proteoglycan splice variants in human tissues by standard in situ hybridization techniques, and Northern blot analysis. Alternatively oligonucleotides with sequences complementary to proteoglycan splice variants could be utilized for therapeutic treatment of amyloid disease, for example antisense RNA using RNA interference techniques.

The oligonucleotides of the present invention may be in the form of RNA or in the form of DNA, which DNA includes cDNA, genomic DNA, and synthetic DNA. The DNA may be double-stranded or single-stranded, and if single-stranded may be the coding strand or non-coding (anti-sense) strand. The coding sequence which encodes the mature polypeptide may be identical to the coding sequence shown or may be a different nucleotide sequence as a result of the redundancy or degeneracy of the genetic code, encodes the same mature polypeptide as the DNA or the cDNA.

In another aspect, this invention is the production of new animal models for the production, deposition, accumulation and/or persistence of fibrillar Aβ amyloid in brain as observed in Alzheimer's disease and Down's syndrome. These new animal models can also be used to effectively screen and identify new therapeutic agents that target fibrillar Aβ amyloid formation, deposition, accumulation and/or persistence in brain.

In another aspect, this invention is the utilization of new animal models for the production, deposition, accumulation and/or persistence of fibrillar amyloid as observed in each of the other amyloidoses. These new animal models can also be used for the evaluation of candidate drugs and therapies for the prevention and treatment of the amyloidoses as referred to above.

In another aspect, this invention is the production and utilization of new transgenic animals that overexpress or knock-out a particular proteoglycan splice variants in an effort to produce specific phenotypes associated with a disease and/or pathological processes, including, but not limited to, Alzheimer's disease and/or other amyloid diseases.

In yet another aspect of the invention, syndecan-2 variant plasmids could be constructed using knowledge and materials known to one skilled in the art and can be used for Northern blot analysis of mRNA derived from human tissues, cells, and/or cells in biological fluids to further determine the size of transcripts. In addition, Northern blots utilizing the same probes of the invention can be utilized to quantitate relative levels of syndecan-2 splice variant mRNA in tissues from normal patients in comparison to those with specific diseases (such as the amyloid diseases).

In yet another aspect of the invention, fragments of the full length gene may be used as a hybridization probe for a cDNA library to isolate the full length gene and to isolate other genes which have a high sequence similarity to the gene or similar biological activity. The probe may also be used to identify a cDNA clone corresponding to a full length transcript and a genomic clone or clones that contain the complete syndecan-2 splice variant gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Another aspect of the invention relates to vectors which includes polynucleotides as described herein, host cells which are genetically engineered with vectors of the invention and the production of polypeptides of the invention by recombinant techniques. Host cells are genetically engineered (transformed or transduced or transfected) with the vectors of the invention which may be, for example, a cloning vector or an expression vector. The vector may be, for example, in the form of a plasmid, a viral particle, a phage etc. The engineered host cells can be cultured in conventional nutrient media modified as appropriate for activating promoters, selecting transformants or amplifying the genes. The culture conditions, such as temperature, pH and the like, are those previously utilized with the host cell selected for expression, and will be apparent to those ordinarily skilled in the art.

In another aspect of the invention, the polynucleotides of the present invention may be employed for producing polypeptides by recombinant techniques. For example, the polynucleotides may be included in any one of a variety of expression vectors for expressing a polypeptide. Such vectors included chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

In accordance with one aspect of the present invention there is provided novel peptide sequences encoded within the new syndecan-2 splice variants described herein, as well as biologically active and diagnostically or therapeutically useful fragments, analogs and derivatives thereof. The peptide sequences described in the present invention are human sequences.

In accordance with another aspect of the present invention, there is provided a process for diagnosing Alzheimer's disease or a susceptibility to Alzheimer's disease related to under-expression or over-expression of the polypeptide product of a splice variant. The process comprises determining a mutation in a nucleic acid sequence encoding the splice variant which is responsible for the under-expression or over-expression of the polypeptide translated from the splice variant.

The present invention accordingly encompasses the expression of a syndecan-2 splice variant polypeptide, in either prokaryotic or eukaryotic cells, although eukaryotic expression is preferred. Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cells or tissue is of human, primate, hamster, rabbit, rodent, cow, pig, sheep, horse, goat, dog, or cat origin, but any other mammalian cell may be used.

The polynucleotides of the present invention may be utilized as research reagents and materials for discovery of treatments and diagnostics to human diseases.

These and other features and advantages of the present invention will become more fully apparent when the following detailed description of the invention is read in conjunction with the accompanying figures.

BRIEF DESCRIPTION OF THE DRAWINGS

The following drawings are illustrative of embodiments of the invention and are not meant to limit the scope of the invention.

FIG. 5 shows the putative amino acid sequence of Syn2-vE1a (SEQ ID No.: 7)which contains an in-frame 52-residue insertion (grey) that codes for four extra SG sites (bold and underlined), including a prominent adjacent duplicate SG sequence flanked by acidic residues.

DETAILED DESCRIPTION OF THE INVENTION

Figure 1:
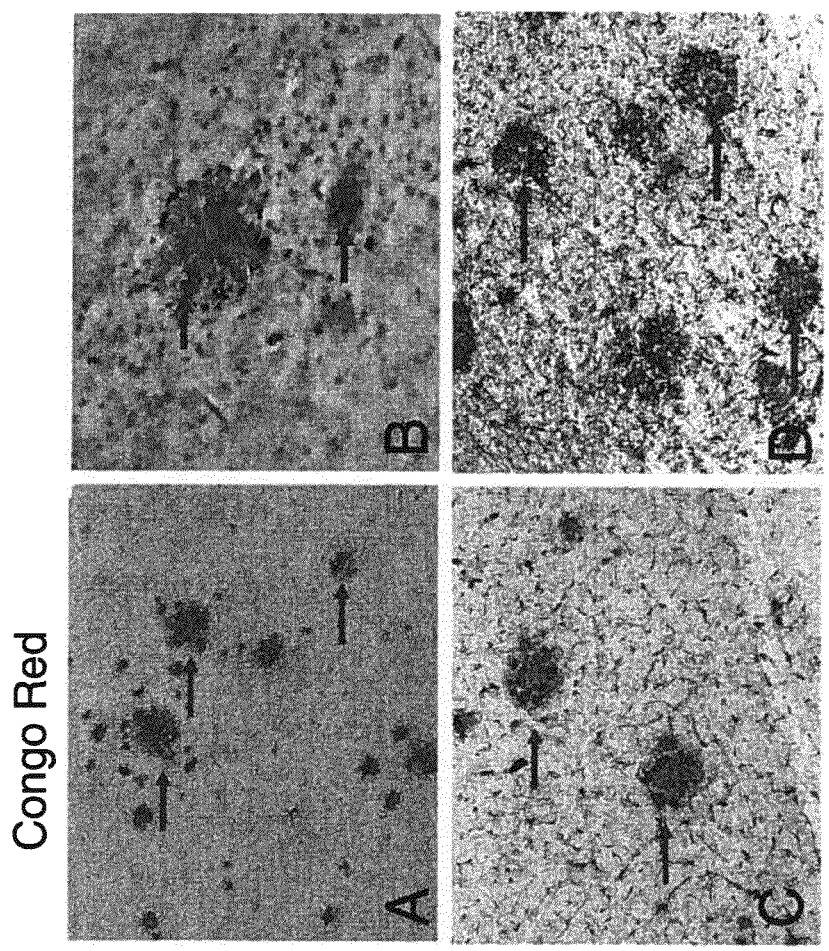
FIG. 1: are photomicrographs showing that (A) Congo Red, (B) Perlecan, (C) Syndecan-2 and (D) Agrin immunostain Amyloid Plaques in Tg2576 Transgenic Mouse Brain.

Our studies indicate that various PGs are present in AD lesions, including perlecan, syndecan-2, glypican and agrin. FIG. 1: shows in photomicrographs that Perlecan, Syndecan-2 and Agrin immunostain the Amyloid Plaques in Tg2576 Transgenic Mouse Brain. A) Congo red staining of amyloid plaques (arrows) in cortex of 12-month old Tg2576 transgenic mouse X200. B) Perlecan immunostain of amyloid plaques (arrows) in cortex of a 12-month old Tg2576 transgenic mouse X200. C) Syndecan-2 immunostain (mouse monoclonal antibody) of amyloid plaques (arrows) in cortex of 12-month old Tg2576 transgenic mouse (counterstained with Congo red) X200. D) Agrin immunostain (agrin-33 antibody) in thalamus in a 12-month old Tg2576 transgenic mouse (counterstained with Congo red). Agrin deposits are brown, whereas fibrillar amyloid is red X100. PGs may additionally consist of important splice variants that are unique and contain increased GAG chain numbers (and increased sulfation).

Our studies show that some HSPGs identified are present in AD lesions, including perlecan, syndecan-2, glypican and agrin additionally consist of important splice variants that are unique HSPGs with increased GAG chain numbers (and increased sulfation). The generation of such HSPG splice variants is hypothesized to be critical for AB amyloid fibril and PHF formation and persistence. We have identified a syndecan-2 splice variant that may contain up to 7 GAG chains in the variant as compared to 3 GAG chains found normally on the syndecan-2 core protein. The studies described are believed to have both therapeutic and diagnostic implications. The surprising discovery of unique proteoglycan splice variants that may contain additional HS GAG chains (and thus increased sulfation that drives both AB amyloid and PHF formation), further implicate their importance in plaque and tangle development in AD. Identification of novel splice variants that may be also present in blood and/or CSF and that are indicative of amyloid plaque or NFT formation in brain will also have exciting diagnostic implications.

Definitions

In this application, the following terms shall have the following meanings, without regard to whether the terms are used variantly elsewhere in the literature or otherwise in the known art.

A 'splice variant' refers to mRNA (or corresponding cDNA) that arises from an alternative splicing event. Alternative splicing may arise due to changes at the genomic level or during RNA processing. Regardless of how it occurs, alternative splicing results in the insertion or deletion of nucleic acids in the mRNA relative to the wild type. In general, splice variants can generate both in-frame and frame-shift amino acid changes. Translation of a splice variant can result in a polypeptide with an amino acid sequence distinct from the wild type peptide resulting from conventional splicing, provided that the addition or deletion of nucleic acids are in frame. Translation of a splice variant could also result in a truncated polypeptide where a stop codon is introduced.

With respect to splice variants, 'a fragment thereof' refers to nucleic acid or amino acid sequences which are comprised of at least a portion of the splice variant sequence or a portion of the polypeptide sequence translated from the splice variant, that is novel relative to the wild type. Such a fragment thereof may additionally include portions of the wild type mRNA or wild type polypeptide sequence resulting therefrom.

EXAMPLE 1

Identification of a Syndecan-2 Splice Variant with 4 Additional Gag Chains

Figure 2:
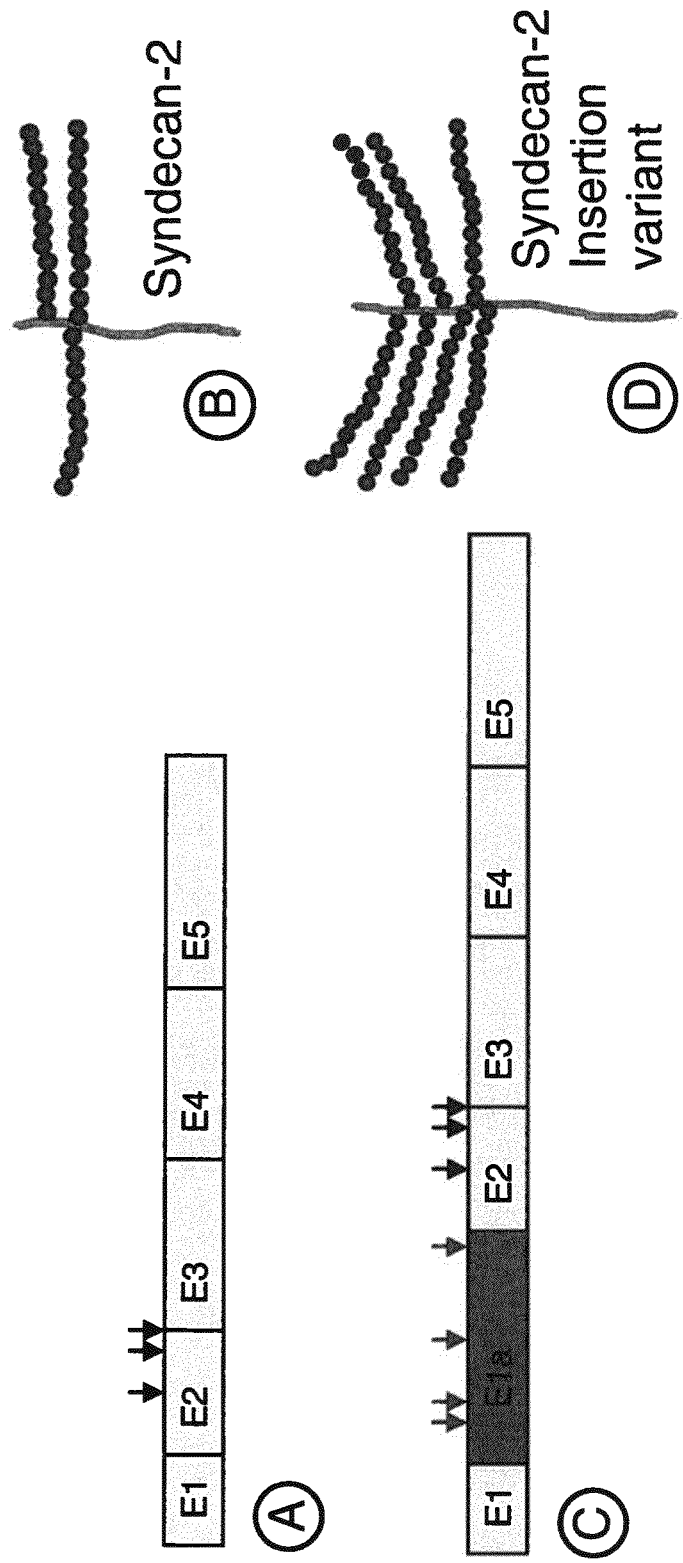
FIG. 2A and C are is a schematic representations of the Exon Structure of Syndecan-2 (A) and the Newly Identified Syndecan-2 Splice Variant (C) Containing Consensus Sequence for 4 Additional GAG Chains.
FIG. 2B and D are diagrams of the tertiary protein structure of Syndecan-2 (B) and the Newly Identified Syndecan-2 Splice Variant (D) Containing Consensus Sequence for 4 Additional GAG Chains.

A novel syndecan-2 splice variant that consists of an exon insertion coding for 4 extra GAG-chain attachment sites was found using a comprehensive bioinformatic approach (SEQ ID NO:8). Initially, we identified the 5' partial sequences of an inserted exon in Syndecan-2 from the Alternative Splicing and Transcript Diversity database (ASDT). The database consists of computationally delineated alternative splicing events as well as literature-based alternative splicing data; it has been integrated with the Ensemble genome database. Electronic hybridization using the 5' partial sequences of the inserted exon as an electronic probe was performed. The analysis led to discovering an EST (Expressed sequence tag) clone (BG195558) from the human EST database at NCBI (National Center of Biotechnology Information). The EST clone contains the sequences for the entire inserted exon as well as downstream exons. Electronic hybridization using the entire inserted exon as an electronic probe against the sequences of human syndecan-2 gene (Gene ID: ENSG00000169439) was then conducted. The results confirmed that the insertion was derived from the middle of intron 1 of this gene, and that the novel splice sites were in compliance with the canonical GT/AG. We therefore named the novel splice variant: syndecan-2 variant E1a (Syn2-vE1a). Syndecan-2 normally consists of a ~22 kDa core protein encoded by 5 exons. Compared to the syndecan-2 transcript Reference Sequence (RefSeq; ENSP00000307046), the novel syndecan-2 splice variant has an exon insertion (E1a) that is in-frame with the downstream codons (FIG. 2A, SEQ ID NO: 6). Protein sequence analysis indicates that the inserted exon codes for an extra 52 residues including four additional putative GAG attachment sites including the adjacent duplicate SG sequence flanked by acidic residues (SEQ ID NO: 9). Ser-Gly consensus sequence for 4 additional GAG attachment sites is shown by red arrows in FIG. 2C. The identified syndecan-2 (Syn2-vE1a) splice variant therefore encodes for a putative HSPG containing a core protein with potentially 7 GAG chains attached (FIG. 2D), instead of 3 GAG chains found normally on syndecan-2 (FIG. 2B)

EXAMPLE 2

Detection of Splice Variants in Alzehimer's Disease Brains

To demonstrate expression of the novel syndecan-2 splice variant (Syn2-vE1a), characterized by comprehensive bioinformatic analyses, in cell cultures and brain tissues, we performed RT-PCR analysis, followed by DNA sequencing. In addition, we also performed semi-quantitative RT-PCR analysis to examine expression levels of the variant in Alzheimer disease (AD) and age-matched control brain samples.

Figure 3:
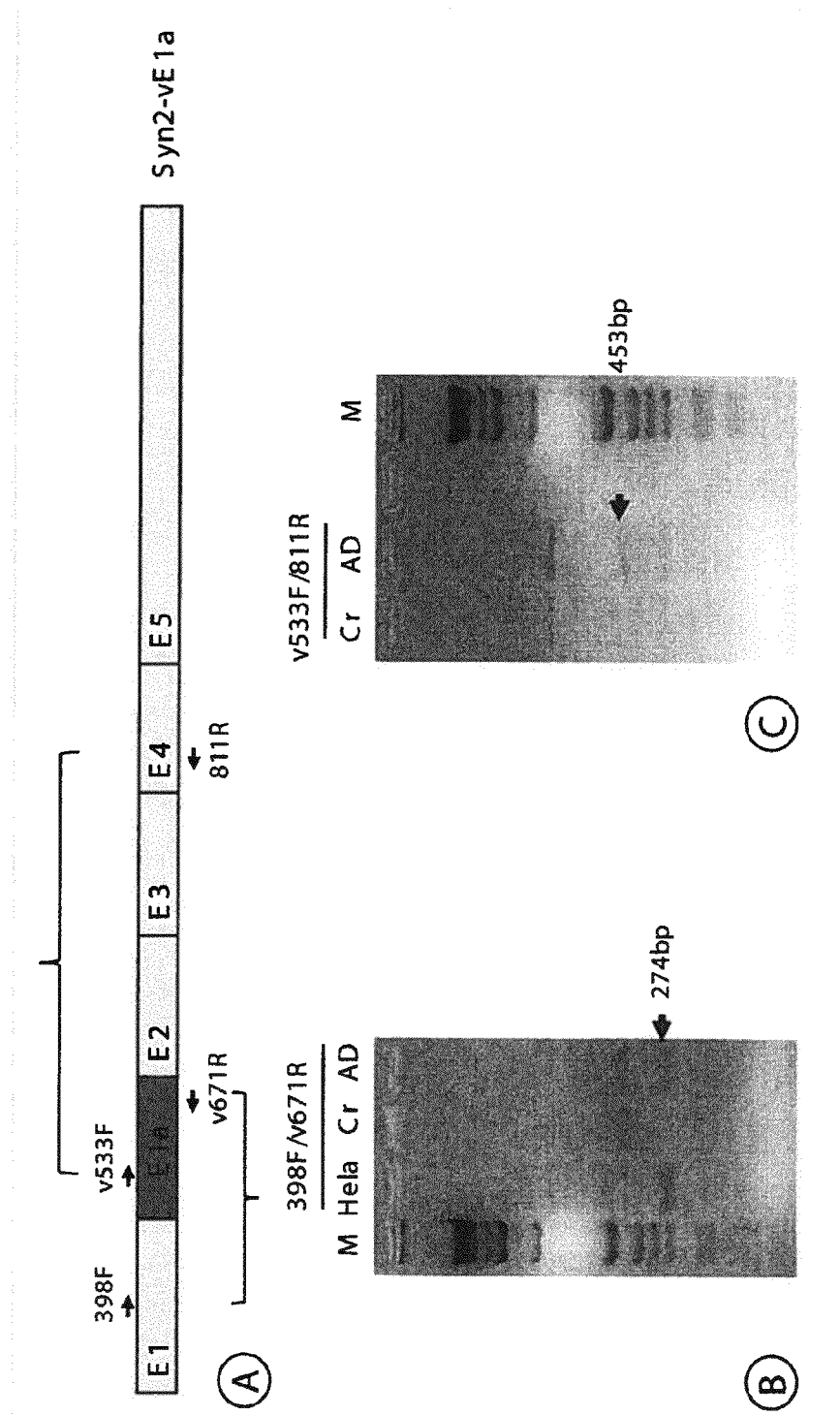
FIG. 3A is a schematic representation of the syndecan-2 splice variant, Syn2-vE1a showing the approximate locations of the primers utilized for PCR.
FIG. 3B is a photograph of PCR products separated by gel electrophoresis using primers 398F and v671R.
FIG. 3C is a photograph of PCR products separated by gel electrophoresis using primers v533F and 811R.

Two total RNA pools were used for these experiments: (1) the AD pool, derived from the middle temporal cortex of seven neuropathologically confirmed late onset AD patients, and (2) the control pool, derived from the corresponding brain region of six age-matched non-demented controls. In addition, total RNA isolated from Hela cells was also analyzed in some experiments. Two micrograms of total RNA from each of the brain samples was first reverse transcribed to single strand cDNA with random hexamers. The single strand cDNA products were then pooled together for downstream PCR analysis. PCR reactions were initially performed with two sets of primers 398F/v671R (SEQ ID NO:1/ SEQ ID NO:3) and v533F/811R (SEQ ID NO:2/SEQ ID NO:4) as shown in FIG. 3A. Primers v671R (SEQ ID NO:3) and v533F (SEQ ID NO:2) were designed to the sequences unique to exon E1a. PCR amplification with 35 cycles revealed DNA bands with the predicted sizes of 274 bp with primer set 398F/v671R (SEQ ID NO:1/SEQ ID NO:3) (FIG. 3B, indicated by an arrow) and 453 by with primer set v533F/811R (SEQ ID NO:2/SEQ ID NO:4) (FIG. 3C, indicated by an arrow). These DNA bands were not observed in negative controls (data not shown). The 274 by (FIG. 3B) and 453 by (data not shown) PCR products were also detected in the RNA sample derived from Hela cells. These results indicate that Syn2-vE1a is expressed in human brain tissues and Hela cell cultures. In addition, the amplified Syn2-vE1a DNA bands appeared to be relatively enriched in the pooled AD sample when compared to those in the pooled control sample, suggesting a possibility of up-regulated expression of this variant in AD brain tissues.

Figure 4:
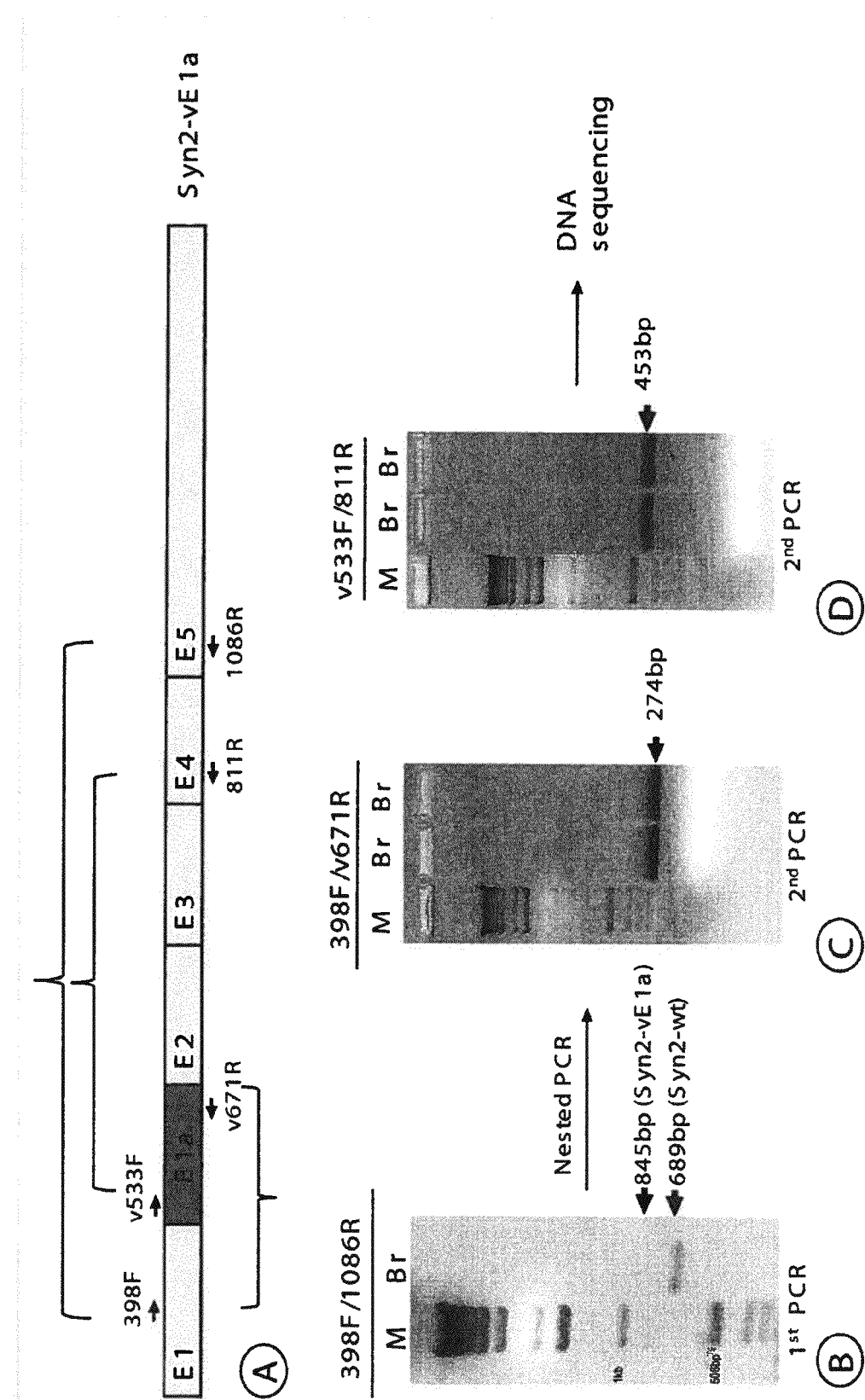
FIG. 4A is a schematic representation of the syndecan-2 splice variant, Syn2-vE1a showing the approximate locations of the nested primer sets to enrich PCR products for DNA sequencing.
FIG. 4B is a photograph of $1^{st}$ round PCR products separated by gel electrophoresis using primers 398F and 1086R.
FIG. 4C is a photograph of $2^{nd}$ round nested PCR products separated by gel electrophoresis using nested primer sets 398F and v671R.
FIG. 4D is a photograph of $2^{nd}$ roundnested PCR products separated by gel electrophoresis using nested primer sets v533F and 811R.

To further confirm expression of Syd2-vE1a in human brain tissues, and to enrich PCR products for DNA sequencing, nested PCR analysis was also performed (FIG. 4). The 1$^{st}$ round of PCR was conducted for 35 cycles with primers 398F (SEQ ID NO:1) and 1086R (SEQ ID NO:5) (FIG. 4B). The 1$^{st}$ round PCR products were then diluted at 1:50, and subjected to two separate 2$^{nd}$ round nested PCR analysis. The nested primer set of 398F/v671R (SEQ ID NO:1/SEQ ID NO:3) produced a 274 by product shown in FIG. 4C. The nested primer set of v533F/811R (SEQ ID NO:2/SEQ ID NO:4) produced a 453 bp product shown in FIG. 4D. As the 1$^{st}$-round primers 398F (SEQ ID NO:1) and 1086R (SEQ ID NO:5) were overlapped with the sequences that were potentially common to both syndecan-2 reference transcript (Syn2-wt) and splice variant Syn2-vE1a, they might amplify both Syn2-wt and Syn2-vE1a, with expected sizes of 689 bp and 845 bp, respectively (FIG. 4B). Although levels of Syn2-vE1a appeared to be low or below the detection limit in the 1$^{st}$ round PCR (FIG. 4B), the nested PCR specifically enriched the Syn2-vE1a amplicons to the levels that were sufficient for DNA sequencing (FIG. 4C&D). In addition, because the 1$^{st}$ round PCR was amplified with primer set that embraces all six exons including exon E1a, the splice variant Syn2-vE1a may also contain all those exons present in the Syn2-wt transcript in addition to the E1a insertion.

EXAMPLE 3

DNA Sequence Analysis of splice Variant Syn2-vE1A

To determine the DNA sequence of Syn2-vE1a, we purified the 274 bp and 453 bp cDNA bands (FIG. 4C&D) with a gel extraction kit (QIAGEN, and performed DNA sequencing on the purified samples with both forward and reverse primers using a commercial DNA sequencing facility. The DNA sequencing results confirmed that the sequences of these major PCR products were identical to those predicted sequences derived from the bioinformatic analysis. The amino acid sequence of splice variant Syn2-vE1a is shown in FIG. 5 (SEQ ID NO:7). We have confirmed that Syn2-vE1a (SEQ ID No.: 7) contains an in-frame 52 amino acid residue insertion that codes for four extra SG sites, including a prominent adjacent duplicate SG sequence flanked by acidic residues. Such motifs are most likely to serve as attachment sites for glycosaminoglycan side chains on a heparan sulphate proteoglycan core protein (Zhang L et al. J Biol Chem. 270: 27127, 1995).

EXAMPLE 4

Comparison of Relative Levels of Splice Variant Syn2-vE1A RNA in Brain

Figure 6:
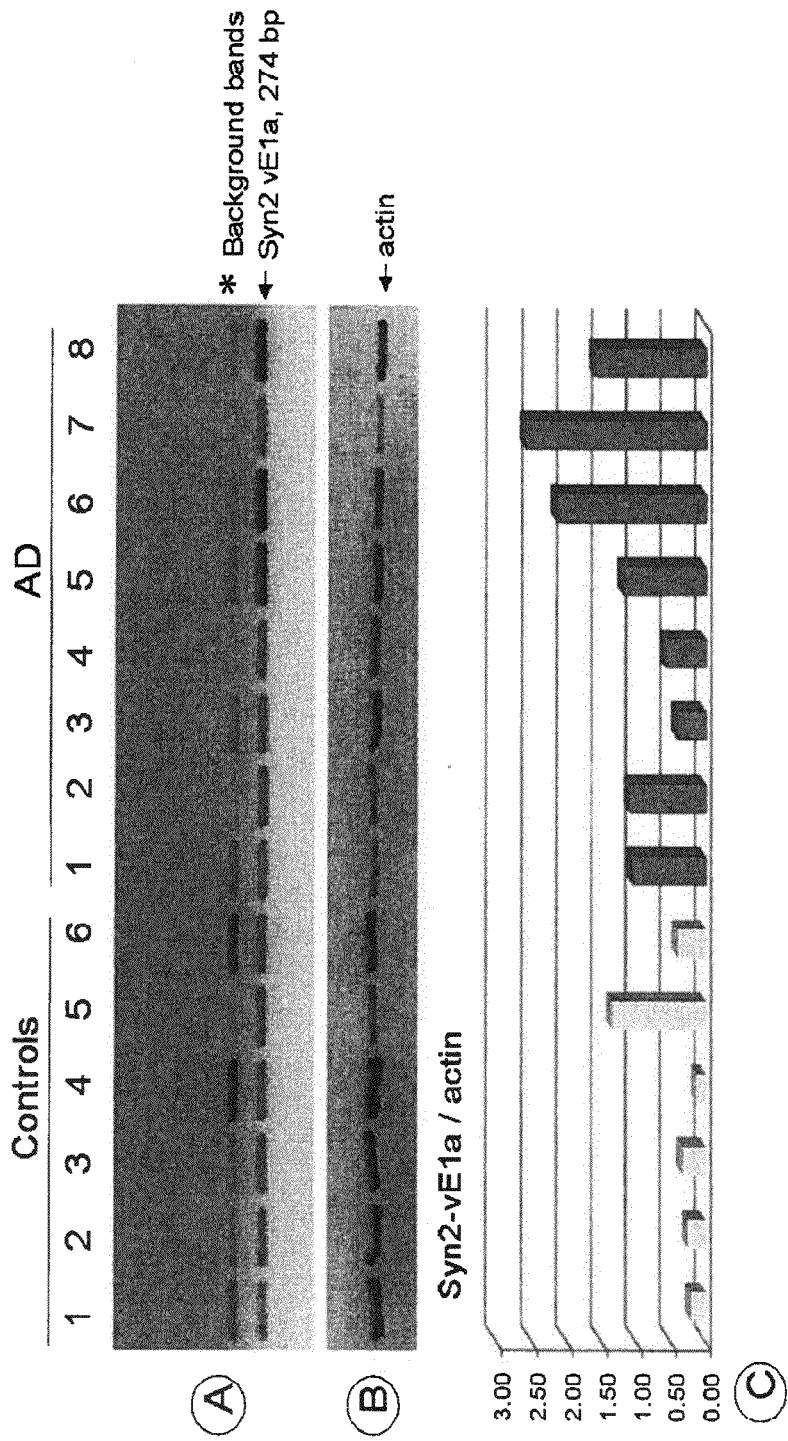
FIG. 6A is a photograph of semi-quantitative PCR products using unpooled single strand cDNA samples reverse transcribed from RNA isolated from middle temporal cortex of late onset AD patients, and age-matched non-demented controls.
FIG. 6B is a photograph of semi-quantitative PCR product control experiment showing amplification products from β-actin
FIG. 6C is a schematic representation of ratios of the DNA band image from FIG. 6A and 6B digitally documented, and quantified with ScionImage software. Relative levels of Syn2-vE1a were normalized to those of β-actin (FIG. 6B).

To determine relative levels of Syn2-vE1a mRNA in AD vs. control brain tissues, we performed semi-quantitative PCR analysis using unpooled single strand cDNA samples reverse transcribed from RNA isolated from middle temporal cortex of late onset AD patients, and age-matched non-demented controls (FIG. 6). The 398F/v671R (SEQ ID NO:1/ SEQ ID NO:3) primer set was used for PCR analysis of Syn2-vE1a with 35-cycle amplification (FIG. 6A). As a control, a 25-cycle PCR amplification of β-actin was also performed in parallel (FIG. 6B). The PCR products were resolved on 2% agarose gels. DNA band images were digitally documented, and quantified with ScionImage software. Relative levels of Syn2-vE1a were normalized to those of β-actin for potential variations due to sample loading and PCR amplification efficiency. Consistent with our previous results, the preliminary quantitative results showed that expression of Syn2-vE1a appeared to be up-regulated in AD brain tissues in the majority of samples. The results indicate that increased expression of Syn2-vE1a coincides with development of AD.

EXAMPLE 5

Cloning of Syndecan-2 Variant E1A (Syn2VE1A) into a Mammalian Expression Vector Total RNA was isolated from human adult non-demented frontal tissues obtained at autopsy from the University of Washington ADRC Brain Bank and immediately frozen at 80° C. Single stranded cDNA was synthesized using M-MLV Reverse Transcriptase (Invitrogen; Carlsbad, Calif., USA) and random priming with hexameric primers (Invitrogen). All other primers used were also synthesized by Invitrogen. Mammalian expression constructs, pcDNA3.1-Syn2WT and pcDNA3.1-Syn2vE1a, were generated as follows. pcDNA3.1-Syn2WT contains the cDNA sequence coding for the human full-length syndecan-2 (REFSEQ mRNA: NM_002998.3). pcDNA3.1-Syn2vE1a contains the cDNA sequence coding for the human full-length Syn2vE1a, (SEQ ID NO: 6). Both cDNA inserts were amplified from human brain single stranded cDNA by PCR with a forward primer, 5'CAGGAGGCTTCGTTTTGC (Synd398-F, SEQ ID NO:1), and a reverse primer, 5'TAGAGACACTAAGTTG-GAG (Synd1086-R, SEQ ID NO: 5). The PCR products were then cloned into a pDrive-UA cloning vector (QIAGEN; Valencia, Calif., USA) as instructed by the manufacturer to generate pDrive-Syn2WT, and pDrive-Syn 2vE1a, respectively. The Syn2WT and Syn2vE1a inserts were then released by EcoRI digestion of pDrive-Syn2WT and pDrive-Syn2vE1a, gel-purified with a gel extraction kit (QIAGEN) as instructed, and subcloned into a pcDNA3.1 vector at EcoRI sites to generate pcDNA3.1-Syn2WT and and pcDNA3.1-Syn2vE1a, which are driven by a cytomegalovirus immediate-early promoter. All inserted cDNA sequences were confirmed by DNA sequencing.

Expression of these constructs were shown in FIG. 7, and described in Example 7 below.

EXAMPLE 6

Production of Polyclonal Antibodies Against Unique Amino Acid Sequence in Syndecan-2 Variant E1A (Anti-Syn2VE1A)

The unique amino acid sequence of Syn2vE1a (SEQ ID NO:7) was analyzed to determine which specific region would be useful for custom peptide synthesis and the generation of polyclonal antibodies (Invitrogen). Computer algorithms to determine the immunogenicity of different peptide regions included the Kyte/Doolittle model of hydrophilicity, and determinations of peptide regions for indices of flexibility, protein surface probability, amphiphilicity, and favorable secondary structure were used. A segment of 16 amino acids corresponding to "GIRRAPLYKRHPTGTA" (amino acids 50-65 of SEQ ID NO: 7) was picked for antibody production due to overall computer index, favorable secondary structure, peptide location, and posttranslational modifications (not overlapped with potential GAG- attachment sites). The region has shown no homology to other proteins using an advanced-PBAST search on peptide sequences through the NCBI genome database. Peptide synthesis, purification and site directed KLH conjugation were performed by Invitrogen. For site directed KLH conjugation a segment of 16 amino acids (amino acids 50-65 of SEQ ID NO: 7) of the Syn2vE1a (SEQ ID NO: 7) peptide was synthesized and a cysteine residue (C) was added to the N-terminus for single point, site-directed conjugation to KLH. This conjugated peptide was used to immunize rabbits for polyclonal anti-peptide antibody production.

Two rabbits were immunized with the above peptide for polyclonal antibody production. Rabbit pre-immune serum, and serum obtained following peptide immunization were then tested by ELISA, utilizing the specific peptide sequence described above. The ELISA data indicated very good, peptide specific antibody titers (not shown).

Eight-week post-immunization antisera from each rabbit was tested by Western analysis for antibody specificity (as described below). The terminal bleed from both rabbits was combined (70-80 ml total), as both antisera showed similar specificity and affinity. The antisera was affinity-purified by Invitrogen using epitope peptide (described above) affinity chromatography. Purified antibodies were dialyzed against 1×PBS, reconstituted at the concentration of 1 mg/ml (containing no preservatives), were aliquoted and stored at −80° C.

EXAMPLE 7

Specificity of Anti-Syn2vE1A as Assessed by Western Analysis

Specificity of polyclonal anti-Syn2vE1a antibodies were tested by Western analysis of lysates of human HEK293E cell cultures that were transiently transfected with pcDNA3.1, pcDNA3.1-Syn2WT, and pcDNA3.1-Syn2vE1a.

Human Embryonic Kidney (HEK) 293E cells (CRL-10852; ATCC) were cultured in a regular growth media (RGM) that contained Dulbecco's Modified Eagle Medium (DMEM) (Invitrogen) supplemented with 10% fetal bovine serum at 37° C. in a cell culture incubator supplemented with 5% $CO_2$. A 0.25% trypsin/0.03% EDTA solution was used to release cells from culture dishes. For transient transfection, HEK293E cells were grown to 80-90% confluence in 6-well plates, and transfected with pcDNA3.1, pcDNA3.1-Syn2WT, or pcDNA3.1-Syn2vE1a. Transfection was mediated by polyethylenimines (PEI) (Polysciences, Inc.) as described by Hu et al. (J Biol Chem. 2005, 280:12548). Three micrograms of plasmid DNA and 15 μl of PEI (1 mg/ml in $H_2O$) were used. Eighteen hours after transfection, cells were fed with fresh RGM. Forty-eight hours after transfection cell lysates were collected for Western analysis. Briefly, the cell monolayer was washed once with PBS, and directly lysed in 200 μl of 2× Laemmli sample buffer (75 mM Tris-HCl, pH 8.4, 4% SDS, 20% glycerol, 50 mM DTT, 0.004% bromphenol blue) and iced for 15 min. Lysates were collected into a tube, boiled at 100° C. for 10 min without centrifugation, and stored at −80° C. for Western analysis.

For Western blotting, proteins in lysates were separated in 4-12% Bis/Tris Criterion XT gels (Bio-Rad; Hercules, Calif., USA), with buffer systems recommended by the manufacturer. After electrophoresis, proteins bands were transferred onto Immobilon-PSQ membranes using Bio-Rad Criterion™ Blotters, and a corresponding transfer buffer system (Bio-Rad). Transfer was conducted at 0.4 A (constant) for 90-120 min. All transferred membranes were blocked with 5% milk in PBS+0.05% Tween-20 for 30-60 min at room temperature, and incubated with pre-immune serum (1:20,000), 8-week anti-Syn2vE1a antisera (1:20,000), affinity purified anti-Syn2vE1a antibodies (1:20,000), or a goat polyclonal antibody against syndecan-2 (1:2,000) (sc-9492; Santa Cruz Biotechnology, Santa Cruz, Calif., USA) overnight at 4° C., and then with HRP-conjugated secondary antibody (Vector) at 1:4000 at room temperature for 2 h. Protein bands were visualized with an ECL system (GE Healthcare) by exposing to autoradiography films. For re-probing membranes with a different antibody, membranes were stripped with Restore™ PLUS Western blot stripping buffer (Thermo Scientific; Rockford, Ill., USA), and reprobed with the next primary antibody. PhotoShop was used for image scanning and processing. Quantitation of relative intensities of protein bands on autoradiographic films was performed by image quantification with the ScionImage software downloaded from their corporate website.

For peptide pre-absorption, 20 μl of crude antisera were incubated with the same volume of 3 mg/ml of synthetic epitope peptide provided by Invitrogen at 37° C. for 2 hours, followed by centrifugation at 12,000×g at 4° C. for 15 min. The supernatant was used as peptide pre-absorbed antibodies. For pre-absorbing purified antibodies, 100:1 (peptide:antibody) molar ratio was used.

Figure 7:
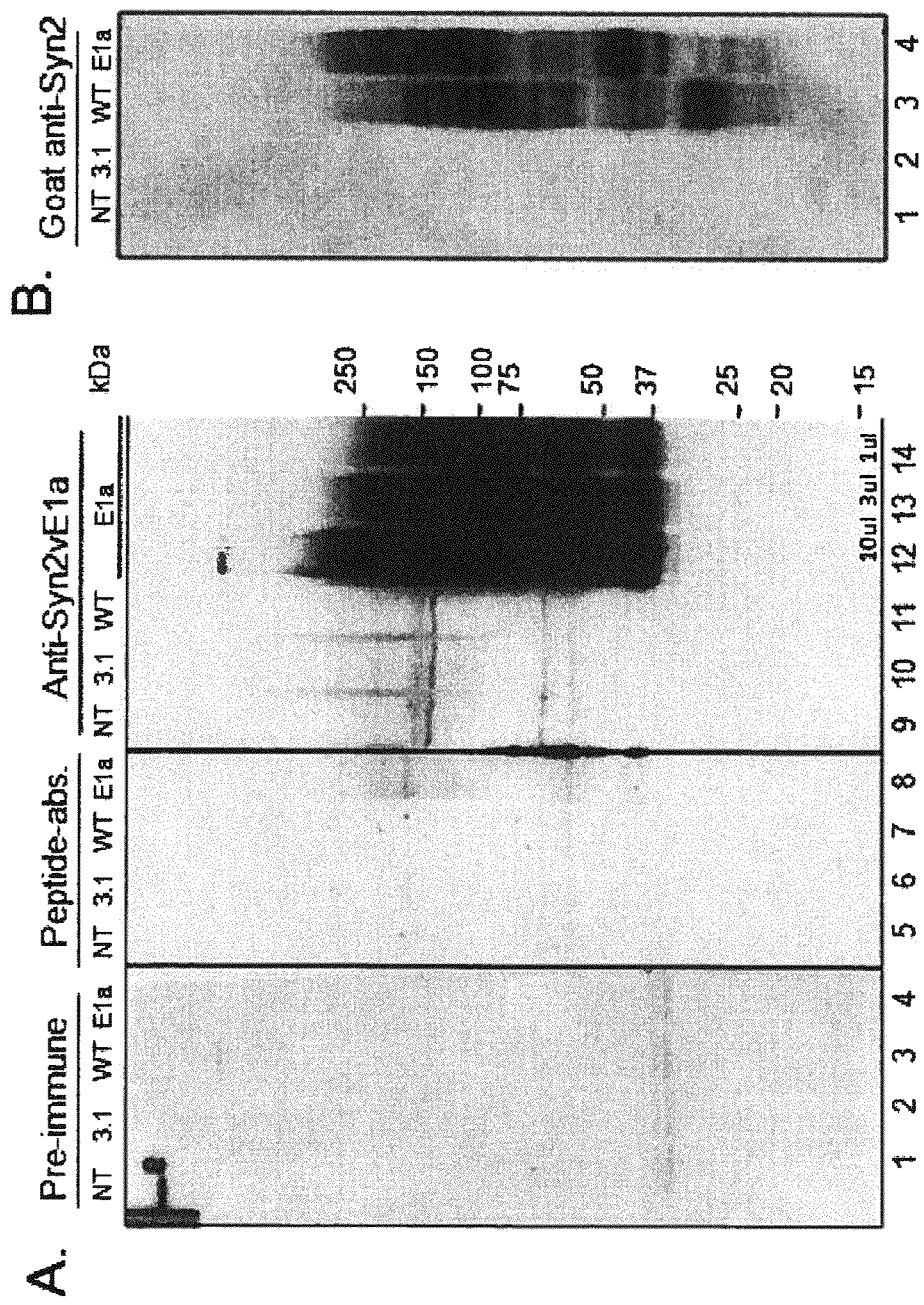
FIG. 7 are photographs of Westerm blots showing the specificity of rabbit polyclonal anti-Syn2vE1a antibodies as assessed by Western analysis and epitope-peptide competition assays.

FIG. 7 shows the specificity of rabbit polyclonal anti-Syn2vE1a antibodies assessed by Western analysis and epitope peptide competition assays. Lysates (10 μl per lane) of HEK293E cell cultures without transfection (NT) or with transient transfection of pcDNA3.1 (3.1), pcDNA3.1-Syn2WT (WT) or pcDNA3.1-Syn2vE1a (E1a) were analyzed by Western analysis, and probed with pre-immune serum (FIG. 7A; lanes 1-4), peptide pre-absorbed 8-week anti-Syn2vE1a antisera (FIG. 7A; lanes 5-8), and unabsorbed 8-week anti-Syn2vE1a antisera (FIG. 7A; lanes 9-14). The results showed that the anti-Syn2vE1a antibody specifically recognized proteins bands ranging from 37-250 kDa (Lanes 12-14; FIG. 7A; lanes 13 and 14 were loaded with reduced amounts of lysates, 3 and 1 μl, respectively). Relatively discrete bands were observed at ~35 kDa and ~70 kDa, which may represent monomers and dimers of Syn2vE1a, respectively. It has been shown that the syndecan family proteins, especially syndecan-2, form strong, detergent-resistant dimers mediated by transmembrane domains (Dews and Mackenzie, Proc Natl Acad Sci USA. 2007, 104:20782). The high molecular-weight smear between 75-250 kDa likely represent GAG-modified Syn2vE1a, as treatment with heparinases I-III/chondroitinase ABC could partially remove the smear (not shown). Importantly, the anti-Syn2vE1a antibody does not cross-react with Syn2WT (lane 11, FIG. 7A). Expressions of the Syn2WT and Syn2vE1a in the lysates were confirmed by Western analysis with a goat anti-syndecan-2 antibody that recognizes both Syn2WT and Syn2vE1a (FIG. 7B). Pre-immune serum did not detect any specific protein bands (FIG. 7A; lanes 1-4). In addition, peptide pre-absorption blocked more that 98% of anti-Syn2vE1a signals (Lane 8, FIG. 7A). Similar results were also seen with affinity-purified anti-Syn2vE1a antibodies (not shown). Together, these results indicate that anti-Syn2vE1a antibody specifically recognizes Syn2vE1a, and does not react with Syn2WT.

EXAMPLE 8

Syn2vE1a Selectively Reduces Secretions of Beta Cleavage Products of APP in HEK293E Cell Cultures as Assessed by Western Analysis Mammalian expression constructs, pcDNA3.1-APP695-myc, were obtained from previous studies described by Yang et al. (J Biol Chem. 2006, 281:4207). pcDNA3.1-APP695-myc contains the cDNA sequence coding for the human full-length APP695 that was inserted at BamHI and EcoRI sites of a pcDNA3.1-myc/His vector (Invitrogen). The vector is driven by a cytomegalovirus immediate-early promoter.

HEK293E cell cultures grown in 6-well plates were transiently co-transfected with pcDNA3.1-APP695-myc and pcDNA3.1, or pcDNA-Syn2vE1a (1.5 µg of each plasmid DNA). The transfection was performed as described above. 48-hr post transfection, conditioned media was collected, and centrifuged at 8000×g for 10 min at 4° C. to remove cell debris. Cell lysates were also collected in 200 µl of 2× Laemmli sample buffer. Proteins in both lysates or conditioned media were separated in 4-12% Bis/Tris Criterion XT gels (Bio-Rad), and incubated with primary antibodies for overnight at 4° C., and with HRP-conjugated secondary antibody (Vector) at 1:4000 at room temperature for 2 h. Membranes were probed for APP with a rabbit polyclonal antibody specifically recognizing the C-terminus of APP695 (amino acids 676-695; Sigma) at 1:50,000, sAPPα with mAb 6E10 at 1:20,000 (Covance), sAPPβ with a polyclonal antibody specific for secreted APPβ at 1:5000 (Covance), β-actin with mAb C4 at 1:200,000 (Sigma), and Syn2vE1a with anti-Syn2vE1a antibody at 1:20,000.

Figure 8:
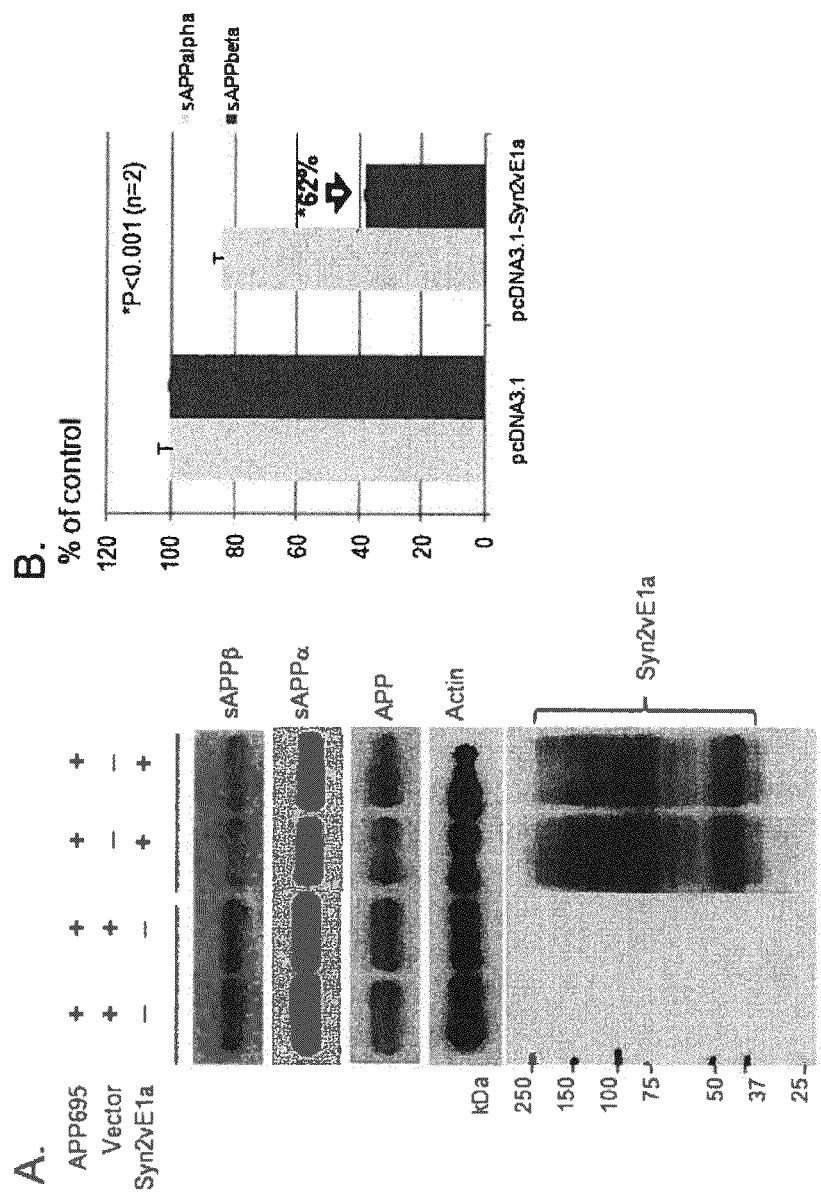
FIG. 8A is a photograph of Western blots showing effects of Syn2vE1a on APP processing in cultured human embryonic kidney 293E (HEK293E) cells overexpressing APP695 and Syn2vE1a as assessed by Western analysis.
FIG. 8B is a graph plotting the densitometry of the Western in 8A.

FIG. 8A shows that co-expression of APP695 with Syn2vE1a reduces levels of secreted APPβ (sAPPβ), a β-cleavage product of APP, in conditioned media of HEK293E cell cultures when compared to co-transfection with pcDNA3.1 (Vector), as assessed by Western analysis. Quantitative densitometry analysis of Western blots revealed a 62% reduction in sAPPβ levels (p<0.001) (FIG. 5B). In contrast, co-transfaction with Syn2vE1a did not significantly alter levels of secreted APPα (sAPPα), an α-cleavage product of APP, and cellular APP (APP) (FIG. 8A-B). The results indicate that Syn2vE1a may selectively affect the β-cleavage pathway of APP.

EXAMPLE 9

Immunolocalization of the Syn2vE1a to the Neurofibrillary Tangles of Alzheimer's Disease Polyclonal anti-Syn2vE1a was then used to immunolocalize the syndecan-2 variant in brains of patients with Alzheimer's disease. Hippocampal sections from an autopsy-confirmed Alzheimer's disease brain obtained from the University of Washington ADRC were utilized. From paraffin embedded material, 6-8 µM serial sections were cut and placed on gelatin coated slides. Amyloid containing plaques and neurofibrillary tangles were identified following Congo red staining (Puchtler et al, Appl Pathol. 3:5-17, 1985) when viewed under polarized light. Detection of Syn2vE1a was achieved using purified anti-Syn2vE1a antibody at a dilution of 1:1000 (FIGS. 9A, 10× magnification; 9B-C, 20× magnification). Controls consisted of staining an adjacent serial section with no primary antibody (FIG. 9E, 20× magnification), or with the purified anti-Syn2vE1a antibody pre-reabsorbed with excess (100× molar ratios) epitope peptide (FIG. 9D, 20× magnification) as described above. Immunostaining of tissue sections was accomplished using the avidin biotin complex (Hsu et al, J. Histochem. Cytochem. 29:577 580, 1981). For immunocytochemical staining the primary antibody was tested at different dilutions to obtain the best specificity with the least background staining. Only the optimal dilutions of primary antibody are reported.

Figure 9:
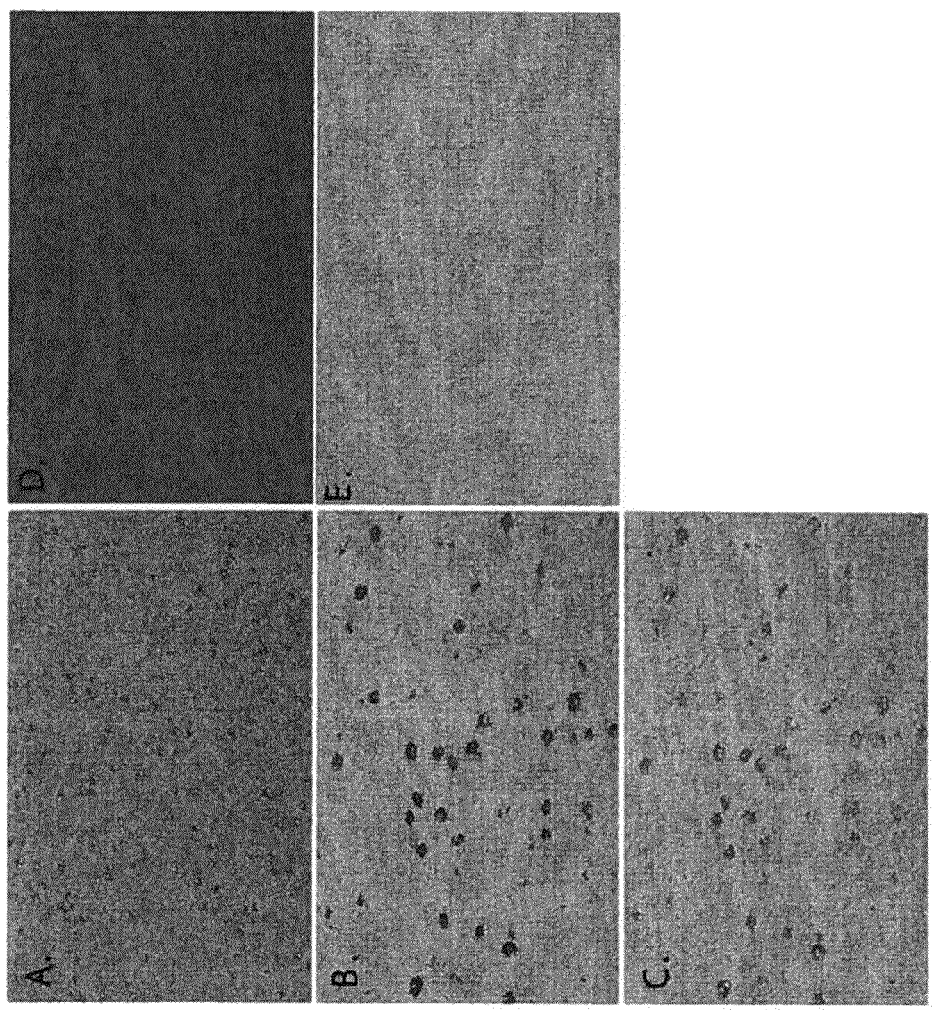
FIG. 9 are photomicrographs showing that the rabbit polyclonal anti-Syn2vE1a antibodies specifically stain pyramidal neurons labeled positive for birefringent tangles in the hippocampus of an Alzheimer brain as assessed by immunehistochemical staining. (A), (B) and (D) are pre-adsorbed with anti-Syn2vE1a (1:1000), (C) is an overlapping image of (B) under birefringent light showing co-localization of label to tangles. (D) and (E) are not treated with primary antibody.

Congo red staining in these tissue sections had previously revealed numerous amyloid plaques and neurofibrillary tangles when stained with Congo red and viewed under polarized light (not shown). The Syn2vE1a antibody revealed staining of pyramidal neurons (FIGS. 9A-B), positive for ghost tangles and intraneuronal tangles which were identified under birefrigent light (FIG. 9C; this is an overlapping image of FIG. 9B viewed under birefrigent lights) or by positive Congo red staining on adjacent serial sections (not shown). Preabsorption experiments completely eliminated any positive immunostaining, indicating the specificity of the antibody used (FIG. 9D). In addition, sections from Alzheimer's disease brains immunostained with preimmune serum did not show any positive immunostaining of neurofibrillary tangles (not shown). This study therefore demonstrated that in Alzheimer's disease brain the syndecan-2 variant E1a (Syn2vE1a) was localized specifically with the neurofibrillary tangles present in brain.

Peptides, Amino Acids and GAGs

The polypeptides referred to in the present invention may be a natural polypeptide, a synthetic polypeptide or a recombinant polypeptide. The fragments, derivatives or analogs of the polypeptides to any of the syndecan-2 splice variants referred to herein may be a) one in which one or more of the amino acid residues are substituted with a conserved or non-conserved amino acid residue and such substituted amino acid residue may or may not be encoded by the genetic code, or b) one in which one or more of the amino acid residues includes a substituent group, or c) one in which the mature polypeptide is fused with another compound, such as a compound used to increase the half-life of the polypeptide (for example, polyethylene glycol), or d) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of the invention.

The polypeptides of the present invention include the polypeptides or fragments therein contained within the deduced amino acid sequences of syndecan-2 splice variant as shown in the sequence listing, as well as polypeptides which have at least 70% similarity (preferably 70% identity) and more preferably a 90% similarity (more preferably a 90% identity) to the polypeptides described above.

Fragments or portions of the polypeptides of the present invention may be employed for producing the corresponding full-length polypeptides by peptide synthesis; therefore, the fragments may be employed as intermediates for producing the full length polypeptides. Fragments of portions of the polynucleotides of the present invention may be used to synthesize full-length polynucleotides of the present invention.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant procedure, the polypeptides of the present invention may be glycosylated or may be non-glycosylated. Polypeptides of the invention may also include an initial methionine amino acid residue.

Syndecan-2 polypeptides of the present invention of can be synthesized according to known method steps, including portions of disclosed new syndecan-2 polypeptides, conservative substitution derivatives thereof or functional derivatives thereof.

Chemical polypeptide synthesis is a rapidly evolving area in the art, and methods of solid phase polypeptide synthesis are well-described in the following references, hereby entirely incorporated by reference (Merrifield, *J. Amer. Chem. Soc.* 85:2149-2154, 1963; Merrifield, *Science* 232: 341-347, 1986; Fields, *Int. J. Polypeptide Prot. Res.* 35, 161, 1990).

Recombinant production of Syndecan-2 polypeptide can be accomplished according to known method steps. Standard reference works setting forth the general principles of recombinant DNA technology include Watson, *Molecular Biology of the Gene*, Volumes I and II, The Benjamin/Cummings Publishing Company Inc., publisher, Menlo Park, Calif. 1987; Ausubel et al, eds., *Current Protocols in Molecular Biology*, Wiley Interscience, publisher, New York, N.Y. 1987; 1992; and Sambrook et al, *Molecular Cloning: A Laboratory Manual*, Second Edition, Cold Spring Harbor Laboratory, publisher, Cold Spring Harbor, N.Y. 1989, the entire contents of which references are herein incorporated by reference.

The polypeptides of the present invention may be utilized as research reagents and materials for discovery of treatments and diagnostics for human diseases.

Diagnostic Applications—Use of Primers and/or Nucleic Acids

The invention provides in one aspect methods of diagnosis of amyloidosis, which method comprises analyzing the expression of the Syndecan-2 splice variants in a sample. In a particular embodiment, the invention provides methods of assaying a sample for splice variants of Syndecan-2 which method comprises, making cDNA from messenger RNA (mRNA) in the sample, amplifying portions of the complementary DNA (cDNA) corresponding to the Syndecan-2 splice variant and detecting the amplified cDNA, characterized in that the amplified cDNA is used in the diagnosis and to monitor the prognosis of the amyloidoses. The sample on which the assay is performed is preferably of body tissue or body fluid. The sample may be a piece of tissue obtained by biopsy, or a fine needle aspirate of cells. Alternatively, it may be a sample of blood or urine or another body fluid, such as a cervical scraping or a non-invasively obtained sample such as sputum, urine or stool.

The primers described can be utilized for the specific detection of Syndecan-2 splice variants in RNA derived from tissues, cells, and/or cells in biological fluids in human tissues using standard RT-PCR methodology, knowledgeable to one skilled in the art.

In addition, the primers can be used for quantitative competitive RT-PCR to determine the quantitative differences in these specific Syndecan-2 variants in total RNA derived from human tissues, cells, white blood cells and/or cells in biological fluids. Changes in quantitative levels of these Syndecan-2 splice variants will aid in the diagnosis and prognosis of patients who demonstrate amyloid and concurrent Syndecan-2 splice variant accumulation in tissues as part of the pathological process in the amyloid diseases. In a preferred embodiment, specific primers are utilized (as described above) for quantitative RT-PCR to determine levels of specific Syndecan-2 splice variants in patients with an amyloid disease in comparison to age-matched controls. The specific syndecan-2 splice variants which are determined to be significantly elevated or diminished in tissues, cells and/or cells in biological fluids in a type of amyloidosis will aid in the diagnosis and monitoring of the prognosis of a given patient afflicted with a particular amyloid disease. Elevated or diminished levels of a particular Syndecan-2 splice variant will be indicative of Syndecan-2 splice variant deposition, accumulation and/or persistence which will correlate with amyloid deposition, accumulation and/or persistence in a given patient. Increasing elevations of a particular Syndecan-2 splice variant in a biopsy or biological fluid sample obtained from a patient at regular intervals (ie. every 6 months) may suggest continued deposition and accumulation of this syndecan-2 splice variant in conjunction with amyloid, implicating a worsening of the disease. Such diagnostic assays as described above may be produced in a kit form.

This invention is also related to the use of the Syndecan-2 splice variant gene as a diagnostic. Detection of a mutated form of Syndecan-2 splice variants will allow diagnosis of a disease or a susceptibility to a disease which results from overexpression or underexpression of Syndecan-2 splice variants. Individuals carrying mutations in the human Syndecan-2 splice variant gene may be detected at the DNA level by a variety of techniques. Nucleic acids for diagnosis may be obtained from a patient's cells, from blood, urine, saliva, tissue biopsy, stool and autopsy material. The genomic DNA may be used directly for detection or may be amplified enzymatically by using PCR prior to analysis. RNA or cDNA may also be used for the same purpose. As an example, PCR primers complementary to the nucleic acids encoding the Syndecan-2 splice variants can be used to identify and analyze mutations. For example, deletions and insertions can be detected by a change in size of the amplified product in comparison to the normal genotype. Point mutations can be identified by hybridizing amplified DNA to radiolabeled Syndecan-2 splice variant RNA or alternatively, radiolabeled Syndecan-2 splice variant antisense DNA sequences. Perfectly matched sequences can be distinguished from mismatched duplexes by RNase A digestion or by differences in melting temperatures.

Sequencing differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags. Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (Myers et al, *Science* 230:1242, 1985). Sequence changes at specific locations may also be revealed by nuclease protection assays, such as RNase and Si protection or the chemical cleavage method (e.g., Cotton et al, *Proc. Natl. Acad. Sci. U.S.A,* 85:4397-4401, 1985). Therefore, the detection of a specific DNA sequence may be achieved by methods such as hybridization, RNase protection, chemical cleavage, direct DNA sequencing or the use of restriction enzymes (e.g., Restriction Fragment Length Polymorphisms (RFLP)) and Southern blotting of genomic DNA. In addition to more conventional gel-electrophoresis and DNA sequencing, mutations can also be detected by in situ analysis.

Yet another aspect of the invention is to make oligonucleotides utilizing the nucleotide sequences described herein, to be utilized as new molecular biological probes to detect Syndecan-2 splice variants in human tissues by standard in situ hybridization techniques, knowledgeable by one skilled in the art. In a preferred embodiment, this includes the utilization of the nucleic acid sequences described Yet another aspect of the present invention is to provide a method which can evaluate a compound's ability to alter (diminish or eliminate) the affinity of a given amyloid protein (as described herein) or amyloid precursor protein, to syndecan-2 splice variant protein or syndecan-2 splice variant-derived GAGs. By providing a method of identifying compounds which affect the binding of amyloid proteins, or amyloid precursor proteins to such syndecan-2 splice variant protein or syndecan-2 splice variant derived-GAGs or fragments thereof, the present invention is also useful in identifying compounds which can prevent or impair such binding interaction. Thus, compounds can be identified which specifically affect an event linked with the amyloid formation, amyloid deposition, and/or amyloid persistence condition associated with Alzheimer's disease and other amyloid diseases as described herein.

In the case in which the amyloid is immobilized, it is contacted with fee syndecan-2 splice variant polypeptides, syndecan-2 splice variant derived-GAGs or fragments thereof, in the presence of a series of concentrations of test compound. As a control, immobilized amyloid is contacted with free syndecan-2 splice variant polypeptides, syndecan-2 splice variant derived-GAGs, or fragments thereof in the absence of the test compound. Using a series of concentrations of syndecan-2 splice variant polypeptides, syndecan-2 spice variant derived-GAGs or fragments thereof, the dissociation constant (IQ) or other indication of binding affinity of amyloid-syndecan-2 splice variant binding can be determined. In the assay, after the syndecan-2 splice variant polypeptides, syndecan-2 splice variant derived-GAGs, or fragments thereof is placed in contact with the immobilized amyloid for a sufficient time to allow binding, the unbound syndecan-2 splice variant is removed. Subsequently, the level of syndecan-2 splice variant-amyloid binding can be observed. This information is used to determine first qualitatively whether or not the test compound can prevent or reduce binding between syndecan-2 splice variant and amyloid. Secondly, the data collected from assays performed using a series of test compound at various concentrations, can be used to measure quantitatively the binding affinity of the syndecan-2 splice variant-amyloid complex and thereby determine the effect of the test compound on the affinity between syndecan-2 splice variant an amyloid. Using this information, compounds can be identified which modulate the binding of syndecan-2 splice variant to amyloid and thereby prevent or reduce the amyloid formation, deposition, accumulation and/or persistence, and the subsequent development and persistence of amyloidosis.

Therapeutic Applications—Use of Primers and/or Nucleic Acids

Another aspect of the present invention is to provide a potential therapeutic using antisense technology. Antisense technology can be used to control gene expression through triple-helix formation or antisense DNA or RNA, both of which methods are based on the binding of a polynucleotide to DNA or RNA. For example, the 5' coding portion of the polynucleotide sequence, which encodes for the mature polypeptides of the present invention is used to design an antisense RNA oligonucleotide of from about 10 to 40 base pairs in length. A DNA oligonucleotide is designed to be complementary to a region of the gene involved in transcription (Lee et al, Nucleic Acids Res. 6:3073, 1979; Cooney et al, Science 241:456, 1988; Dervan et al, Science 251:1360, 1991), thereby preventing transcription by steric blocking and hence the production of syndecan-2 splice variants. The antisense RNA oligonucleotide hybridizes to the mRNA in vivo and blocks translation of the mRNA molecule into syndecan-2 splice variants (Okano, J. Neurochem. 56:560, 1991). The oligonucleotides described above can also be delivered to cells such that the antisense RNA or DNA may be expressed in vivo to inhibit production of the syndecan-2 splice variants.

Alternatively, RNA interference (RNAi) may be utilized to inhibit gene expression via the micro RNA (miRNA) or small interfering RNA (siRNA) pathways. (Song, E et al., Nature Med:347-351, 2003; de Fougerolles, A., et al., Nature Reviews Drug Discovery 6:443-453, 2007; Iorns, E., Nature Reviews Drug Discovery 6:556-568, 2007; and Hammond, S. M., et al., Nature Reviews Genetics 2:110-119, 2001).

The syndecan-2 splice variant polypeptides of the present invention and antagonists which are polypeptides may also be employed in accordance with the present invention by expression of such polypeptides in vivo which is often referred to as "gene therapy". For example, cells from a patient may be engineered with a polynucleotide (DNA or RNA) encoding a polypeptide ex vivo, with the engineered cells then being provided to the patient to be treated with the polypeptide. Such methods are well known in the art. For example, cells may be engineered by procedures known in the art by use of a retroviral particle containing RNA encoding a polypeptide of the present invention.

Preparations of syndecan-2 splice variant polypeptides for parenteral adminstration include sterile aqueous or non-aqueous solutions, suspensions, and emulsions, which may contain auxiliary agents or excipients which are known in the art. Pharmaceutical compositions such as tablets, pills, tablets, caplets, soft and hard gelatin capsules, lozenges, sachets, cachets, vegicaps, liquid drops, elixers, suspensions, emulsions, solutions, syrups, tea bags, aerosols (as a solid or in a liquid medium), suppositories, sterile injectable solutions, sterile packaged powders, can be prepared according to routine methods and are known in the art.

For example, adminstration of such a composition may be by various parenteral routes such as subcutaneous, intravenous, intradermal, intramsclular, intraperitoneal, intranasal, transdermal or buccal routes. Alternatively, or concurrently, adminstration may be by the oral route. Parenteral adminstration can be by bolus injection or by gradual perfusion over time.

A preferred mode of using a syndecan-2 splice variant polypeptides, or pharmaceutical composition of the present invention is by oral adminstration or intravenous application.

A typical regimen for preventing, surpressing or treating syndecan-2 splice variant-related pathologies, such as comprises adminstration of an effective amount of a syndecan-2 splice variant polypeptide, administered over a period of one or several days, up to and including between one week and about 24 months.

It is understood that the dosage of the syndecan-2 splice variant polypeptide of the present invention adminstered in vivo or in vitro will be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

The total dose required for each treatment may be administered by multiple doses or in a single dose. A syndecan-2 splice variant polypeptide may be adminstered alone or in conjunction with other therapeutics directed to syndecan-2 splice variant-related pathologies, such as Alzheimer's disease or amyloid diseases.

Effective amounts of a syndecan-2 splice variant polypeptide or composition are about 0.01 µg to about 100 mg/kg body weight, and preferably from about 10 µg to about 50 mg/kg body weight, such as 0.05, 0.07, 0.09, 0.1, 0.5, 0.7, 0.9., 1, 2, 5, 10, 20, 25, 30, 40, 45, 50, 55, 60, 65, 70, 75, 80, 85, 90, 95 or 100 mg/kg.

Preparations for parenteral adminstration include sterile aqueous or non-aqueous solutions, suspensions, and emulsions, which may contain auxiliary agents or excipients which are known in the art. Pharmaceutical compositions comprising at least one syndecan-2 splice variant polypeptide, such as 1-10 or 1, 2, 3, 4, 5, 6, 7, 8, 9, or 10 syndecan-2 splice variant polypeptides, of the present invention may include all compositions wherein the syndecan-2 splice variant polypeptide is contained in an amount effective to acheive its intended purpose. In adidtion to at least one syndecan-2 splice variant polypeptide, a pharmaceutical composition may contain suitable pharmaceutically acceptable carriers, such as excipients, carriers and/or auxiliaries which facilitate processing of the active compounds into preparations which can be used pharmaceutically.

Pharmaceutical compositions comprising at least one syndecan-2 splice variant polypeptide may also include suitable solutions for adminstration intravenously, subcutaneously, dermally, orally, mucosally, rectally or may by injection or orally, and contain from about 0.01 to 99 percent, preferably about 20 to 75 percent of active component (i.e. polypeptide) together with the excipient. Pharmaceutical compositions for oral adminstration include pills, tablets, caplets, soft and hard gelatin capsules, lozenges, sachets, cachets, vegicaps, liquid drops, elixers, suspensions, emulsions, solutions, and syrups.

Use of Syndecan-2 Splice Variants for Production of New Animal Models—Infusion Models for Alzheimer's Disease and Down's Syndrome Amyloidosis The production of each of the syndecan-2 splice variants in sufficient quantities can also be utilized to produce new animal models of the amyloidoses. For purposes of this application, syndecan-2 splice variants can refer to a) syndecan-2 splice variants which contain both core protein and attached GAG chains, b) syndecan-2 core protein only, or c) syndecan-2 GAG chains derived from syndecan-2 splice variants, or any fragments or combinations of any of the above. For example, as a new model of Alzheimer's disease amyloidosis, syndecan-2 splice variants can be continuously infused in combination with beta-amyloid protein (Aβ) into the hippocampus of groups of rats or mice. In a preferred embodiment syndecan-2 splice variant (25 µg) is dissolved in water in a microcentrifuge tube containing 50 µg of Aβ (1-40) or (1-42). Using the described methods of Snow et al (*Neuron* 12:219-234, 1994) herewith incorporated by reference, the syndecan-2 splice variant+Aβ is continuously infused for 1 week into hippocampus (via stereotaxic surgeries knowledgeable by one skilled in the art) of groups (usually 10) of 3 month old Sprague-Dawley rats. Following the 1 week infusion the animals are sacrificed and the brains are removed as described in Snow et al (*Neuron* 12:219-234, 1994), and 6-8 µm serial sections spanning through the entire infusion site are cut from paraffin embedded blocks or from frozen sections. The extent of amyloid deposition per animal is then detected by Congo red staining (as viewed under polarized light) or Thioflavin S fluorescence and quantitated in a blind study using an arbitrary scoring method as described by Snow et al (*Neuron* 12:219-234, 1994). The use of the syndecan-2 splice variant peptides and/or proteins in this model can be used as a rapid model of fibrillar Aβ amyloid deposition, accumulation and persistence in vivo. In addition, this model may be used to rapidly screen potential therapeutics targeting fibrillar Aβ amyloid formation, deposition, accumulation and/or persistence. In a preferred embodiment, syndecan-2 splice variant+Aβ+therapeutic compound is directly infused into the hippocampus (as described above) of a group of animals and comparisons are made to a group of animals infused with only syndecan-2 splice variant+Aβ. Compounds or drugs found to reduce amyloid formation, deposition, accumulation and/or persistence (as determined by Congo red or Thioflavin S scoring) in vivo are then identified as having potential therapeutic value.

In another preferred embodiment, the potentially therapeutic compound can be tested to reduce amyloid persistence over prolonged periods of time. In this model, groups of animals (usually 10 animals per group) are infused with syndecan-2 splice variant+Aβ+therapeutic compound and directly compared to groups of animals (usually 10 animals per group) infused with syndecan-2 splice variant+Aβ. Following a 1 week infusion (as described above), the cannulae are removed with the animals under anesthesia, and the animals are then allowed to recover until sacrifice 1, 3, 6 or 12 months later. Serial sections are cut and amyloid is scored as described above. It is expected that persistent amyloid deposits can be observed in animals infused with the syndecan-2 splice variant+Aβ. Potent therapeutic compounds will be those that effectively reduce the amount of amyloid observed in comparison to those animals not given the therapeutic compound. These compounds can therefore be referred to as compounds which effectively reduce amyloid persistence in vivo.

In yet another preferred embodiment, potentially therapeutic compounds can be tested for reducing or eliminating pre-formed amyloid deposits. In this model, two groups of animals (usually 10 animals per group) are infused with syndecan-2 splice variant+Aβ. Following a 1 week infusion (as described above), the cannulae and osmotic pumps are changed (with the animals under anesthesia), and a new cannulae connected by vinyl tubing to a new osmotic pump, contains either vehicle only (ie. double distilled water) or the potential therapeutic compound. Following a 1 week continuous infusion of either the vehicle or the potential therapeutic compound of interest, the animals are sacrificed. Serial sections are then cut through the entire infusion site and the extent of amyloid is measured by arbitrary blind scoring as described above. Potent therapeutic compounds will be those that are able to effectively remove pre-formed amyloid deposits. It is anticipated that little to no reduction in the amount of amyloid will be observed in the group of animals infused with vehicle only. These compounds can therefore be referred to as therapeutic compounds which effectively reduce pre-formed amyloid deposits in vivo.

Syndecan-2 Splice Variant Transgenic Animals

In accordance with the disclosure of means and methods of making transgenic animals, in particular transgenic mice, which disclosure is found in U.S. patent application Ser. No. 08/870,987, by K. Fukuchi, A. Snow and J. Hassell, filed Jun. 6, 1997, and which is hereby incorporated by this reference as if fully set forth, another aspect of the invention is to produce new transgenic animals that overexpress or knock-out a particular syndecan-2 splice variant in an effort to produce specific phenotypes associated with a number of diseases and/or pathological processes. For the production of these new syndecan-2 splice variant transgenic animals, this would generally involve ligating the splice variant cDNA sequence from the plasmid clones (described herein) into the correct region of normal human syndecan-2 cDNA (available in an expression vector with correct promoter and enhancer regions as described in the incorporated reference above). The syndecan-2 splice variant expression vector would then be inserted into mouse eggs or embryonic stem cells and transgenic mice would be produced through known, routine methods as described in the incorporated reference above. Production of these transgenic mice, and the mating of these mice with transgenic animals which overexpress a given amyloid protein or its precursor protein, will produce progeny that develop much or all of the phenotypic pathology of a given amyloid disease. The production of new transgenic animal models of amyloid diseases may be used as in vivo screening tools to aid in the identification of lead therapeutics for the amyloidoses and for the treatment of clinical manifestations associated with these diseases (as described in the incorporated reference above). The successful overproduction of syndecan-2 splice variants in transfected cells also serves as a new means to isolate these syndecan-2 splice variants which will meet the increasing demands for use of syndecan-2 splice variants for a variety of in vitro and in vivo assays.

All references cited are herein incorporated by reference.

We claim:

1. A method for the detection and/or quantitation of a splice variant, Syn2-E1a (SEQ ID NO:6), in a biological sample, the method comprising synthesizing cDNA from mRNA in the sample, amplifying the cDNA to the splice variant Syn2-E1a (SEQ NO:6) using PCR and primers SEQ ID NO:2 and SEQ ID NO:3, and detecting and/or quantitating the presence of Syn2-E1a (SEQ ID NO:6) in the amplified cDNA.

2. The method of claim 1 wherein the biological sample is derived from human tissues, cells or biological fluids.

3. The method of claim 2 wherein said biological fluids are selected from the group consisting of blood, plasma, serum, cerebrospinal fluid, sputum, saliva, urine and stool.

4. The method of claim 2 wherein said biological fluid is cerebrospinal fluid.

* * * * *